United States Patent
de Laat et al.

(10) Patent No.: US 11,707,078 B2
(45) Date of Patent: Jul. 25, 2023

(54) SINGLE CELL PROTEIN FROM THERMOPHILIC FUNGI

(71) Applicant: The Protein Brewery B.V., Breda (NL)

(72) Inventors: Wilhelmus Theodorus Antonius Maria de Laat, Breda (NL); Joan Sebastian Gallego Murillio, Delft (NL)

(73) Assignee: The Protein Brewery B.V., Breda (NL)

( * ) Notice: Subject to any disclaimer, the term of this patent is extended or adjusted under 35 U.S.C. 154(b) by 323 days.

(21) Appl. No.: 16/323,782

(22) PCT Filed: Aug. 11, 2017

(86) PCT No.: PCT/EP2017/070470
§ 371 (c)(1),
(2) Date: Feb. 7, 2019

(87) PCT Pub. No.: WO2018/029353
PCT Pub. Date: Feb. 15, 2018

(65) Prior Publication Data
US 2019/0174809 A1 Jun. 13, 2019

(30) Foreign Application Priority Data
Aug. 11, 2016 (NL) ..................................... 2017309

(51) Int. Cl.
| | |
|---|---|
| A23K 10/16 | (2016.01) |
| A23L 31/00 | (2016.01) |
| A23L 33/195 | (2016.01) |
| C12N 1/14 | (2006.01) |
| A23J 1/00 | (2006.01) |
| C12R 1/645 | (2006.01) |
| C12R 1/845 | (2006.01) |

(52) U.S. Cl.
CPC .............. *A23L 31/00* (2016.08); *A23J 1/008* (2013.01); *A23K 10/16* (2016.05); *A23L 33/195* (2016.08); *C12N 1/14* (2013.01); *C12N 1/145* (2021.05); *A23V 2250/54* (2013.01); *C12R 2001/645* (2021.05); *C12R 2001/845* (2021.05)

(58) Field of Classification Search
CPC ....... A23L 31/00; A23L 33/195; C12N 1/145; C12N 1/14; C12R 2001/645; A23K 10/16; A23J 1/008; A23V 2250/54; A23V 2250/546; A23V 2002/00
See application file for complete search history.

(56) References Cited

U.S. PATENT DOCUMENTS 8,484,295 B2    7/2013  Van Leeuwen
2014/0166555 A1* 6/2014  Dibel ..................... B01D 61/20
                                                    210/87

FOREIGN PATENT DOCUMENTS

WO    WO-198401959 A1 *  5/1984  ............... C12N 1/00

OTHER PUBLICATIONS

Reade et al., "High-Temperature Production of Protein-Enriched Feed from Cassava by Fungi". Applied Microbiology Dec. 1975, p. 897-904. (Year: 1975).*
Iyayi et al. Protein enrichment of cassava by-products through solid state fermentation by fungi. J. Food Technol Afr. 2001;6(4):116-118.*
Maheshwari et al. Thermophilic Fungi: Their Physiology and Enzymes. Microbiol Mol Biol Rev. 2000;64(3):461-488.*
UNEP. Technologies for Converting Waste Agricultural Biomass to Energy. UNEP. 2013;1-229.*
Korz et al. Simple fed-batch technique for high cell density cultivation of *Escherichia coli*. Journal of Biotechnology. 1995;39:59-65.*
Reade, A.E. et al. "High-temperature production of protein-enriched feed from cassava by fungi." Applied microbiology 30.6 (1975): 897-904.
Gregory, K. F., et al. "Further thermotolerant fungi for the conversion of cassava starch to protein." Animal Feed Science and Technology 2.1 (1977): 7-19.
Stevens et al "Production of microbial biomass protein from potato processing wastes by Cephalosporium eichhorniae." Applied and environmental microbiology 53.2 (1987): 284-291.
Grajek, W. "Production of protein by thermophilic fungi from sugar-beet pulp in solid-state fermentation." Biotechnology and bioengineering 32.2 (1988): 255-260.
Karapinar et al "The utilisation of citrus waste as substrate for microbial protein production by the fungus Sporotrichum pulverulentum." Journal of Chemical Technology and Biotechnology 32.7-12 (1982): 1055-1058.
Bajpai et al. "Single cell protein production from rayon pulp will waste by Paecilomyces variotii." Journal of fermentation technology 65.3 (1987): 349-351.
Grajek "Cooling aspects of solid-state cultures of mesophilic and thermophilic fungi." Journal of fermentation technology 66.6 (1988): 675-679.
Varavinit et al "Production of Single Cell Protein from Cassava Starch in Air-lift Fermenter by Cephalosporium eichhorniae." Starch-Stärke 48.10 (1996): 379-382.
Mikami et al "Factors affecting yield and safety of protein production from cassava by Cephalosporium eichhorniae." Applied and environmental microbiology 43.2 (1982): 403-411.
SILVA Tony M., et al. "Production of saccharogenic and dextrinogenic amylases by Rhizomucor pusillus A 13.36." Journal of Microbiology (2005): 561-568.

* cited by examiner

*Primary Examiner* — Lynn Y Fan
(74) *Attorney, Agent, or Firm* — N.V. Nederlandsch Octrooibureau

(57) ABSTRACT

The present invention relates to a process for producing single cell protein, wherein a thermophilic fungus is grown a fermentable carbon-rich feedstock at a high temperature and at an acidic pH. This allows for a cost effective fermentation process that can to be run under non-sterile conditions and without additional cooling requirements. The process can be used to convert by-products or waste from agriculture or food production, or organic fractions of municipal solid waste into valuable single cell protein that can be applied as dietary source of protein or protein supplement in human food or animal feed.

19 Claims, 1 Drawing Sheet
Specification includes a Sequence Listing.

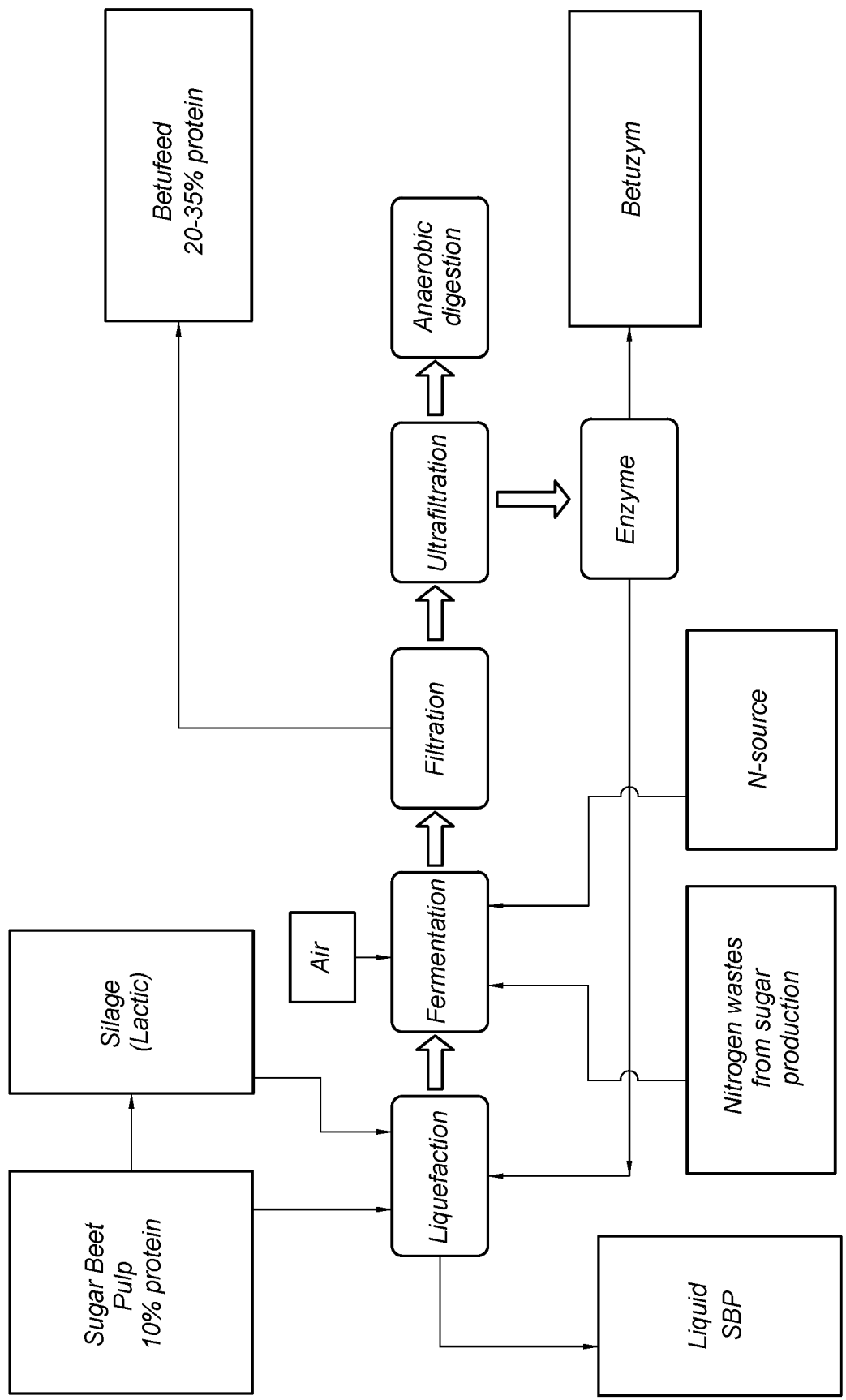

SINGLE CELL PROTEIN FROM THERMOPHILIC FUNGI

FIELD OF THE INVENTION

The present invention relates to the fields of microbiology and fermentation technology. In particular, the invention relates to the production single cell protein for use in food products and animal feed, through fermentation of carbon- and energy-rich feedstocks by thermophilic fungi.

BACKGROUND ART

The increasing global population and wealth leads to rapid increasing demand for protein-rich food like meat, dairy products, insects and fish. As a consequence, the increased production of soybeans in countries like Brazil leads to loss of tropical rain forest in order to enable soybean production on an enormous scale, which is exported to the rest of the world. Therefore there is a need for more local production of protein-rich animal feed. One method for producing protein-rich animal feed is to produce "single cell protein" (SCP) by means of fermentation (Suman et al., 2015, Int J. Curr. Microbiol. Appl. Sci., Vol 4., No 9., pp 251-262). Fermentation in this respect is understood as the microbial conversion of carbohydrate-rich feedstocks into protein-rich products consisting of microbial cells such as bacteria, yeasts or fungi. The use of SCP as animal feed and food ingredient brings the further advantages that microbial cells have a high content of essential amino acids and that microbial cells, e.g. when applied to supplement grain-based diets, produce useful enzymes such as phytase, xylanases, pectinases, proteases, cellulases, amylases, all of which can have a positive effect on digestibility of the compound feeds that have high contents of e.g. the anti-nutritional compound phytate, poorly digestible fibres etc. Furthermore, in particular fungal cells can be very rich in trace elements and vitamins making the fermented feedstuffs very nutritive. Fungi such as e.g. mushrooms are unique in that they contain vitamin B12, which vegetables cannot produce. Since vitamin B12 is mainly of animal origin, deficiency is commonly associated with vegetarian diets. Mushrooms were found to contain 0.32-0.65 mg per gram of vitamin B12, allowing just 3 g of fresh mushrooms to provide the recommended daily allowance of this vitamin. Vegetarians may find this a useful way of getting this important nutrient.

Outila et al. (1999 American Journal of Clinical Nutrition, 69: 95-98) found that ergocalciferol in mushrooms increased serum 25-hydroxy vitamin D concentrations as effectively as did supplements, allowing mushrooms to be reliably recommended as a natural vitamin D source. Pro-vitamin D is present in some mushrooms, particularly shiitake, and can be converted to vitamin D by the ultraviolet irradiation in sunlight. Vitamin A is uncommon although several mushrooms contain detectable amounts of pro-vitamin A measured as the β-carotene equivalent. Most cultivated mushrooms are believed to contain low amounts of the fat-soluble vitamins, K and E, and make only a small contribution to the daily requirement of vitamin C.

Quorn™, a mycoprotein produced by *Fusarium venenatum* contains Vitamin B1 (Thiamin), Vitamin B2 (Riboflavin), Vitamin B3 (Niacin), Vitamin B5 (Pantothenic acid) and Biotin (www.mycoprotein.org). For the purpose of optimization, one could select specific thermophilic fungi to be applied in this process high in vitamins required by the application of feed for Fish, Insects, Chickens, Cows, Pigs, etc. but also for the production of meat replacing substituents in food applications.

One problem in SCP production is the concentration of the SCP-biomass that is produced in the fermentation broth, particularly in the case of submerged fermentations with bacteria or yeasts. Another problem is the need for expensive enzymes to convert the cheap polymeric carbon sources to monomeric fermentable sugars. Furthermore, to avoid infection when using mesophilic microorganisms for SCP production sterile fermentation conditions need be applied, which leads to prohibitive operational costs due to high capital investments and energy demands (Bajpai and Bajpai, 1987, J. Ferment. Technol. 65, 3: 349-351). Some of these issues have been addressed by using solid state fermentation with thermophilic fungi (Grajek, 1987, Biotechnol. Bioengineer. 32: 255-260; and Grajek, 1988, J. Ferment. Technol. 66, 6: 675-679). However, scaling up of such solid state processes poses problems with aeration and cooling.

U.S. Pat. No. 8,481,295B2 discloses the production of thermophilic fungi as animal feed ingredient using batch fermentation on thin stillage from ethanol refineries. However, the fungal strain used therein does not perform well at pH<4 and temperature higher than 45° C., which makes the process sensitive to bacterial and yeast contamination.

Gregory K. F et al. (1977, Anim. Feed Sci. Technol. 2:7-19) disclose attempts to use thermotolerant fungi for the conversion of cassava, in the course of which many thermotolerant fungi were isolated. However, these attempt did not lead to commercialized products as contamination issues remained with their organisms, or undesirable human pathogens were used (e.g. *Aspergillus fumigatus*), while their *Mucor* strains were found to be poorly digestible in rat studies.

Several authors have reported the thermotolerant fungus *Cepalosporium eichornia* for production of SCP. E.g. Stevens et al (1987, Appl Environ Microbiol. 53(2):284-291) disclose the use of *C. eichornia* at pH 3.75 and 45° C., under which conditions they frequently observe bacterial contaminations. Moreover, these authors were unable to obtain growth in settling tank sludge samples. Varavinit et al. (1996, Starch 48: 379-380) produced *C. eichornia* SCP from very diluted cassava (2% dry matter) in an airlift fermenter at pH 3.8 and 45° C., but were never able to commercialize it. Mikami et al (1982, Appl Environ Microbiol. 43(2):403-11) also carry out *C. eichornia* fermentations and show that it was not possible to grow at temperatures higher than 45° C. or at a pH lower than pH 3.8.

Reade and Gregory (1975, Appl Microbiol. 30:897-904) disclose production of SCP using a thermophylic fungi identified as *Aspergillus fumigatus* and demonstrated that at temperature of 45° C. yeast contaminations still occur, which was no longer the case at a temperature of 47° C. However, as *Aspergillus fumigatus* is a human pathogen it is unsuitable for producing SCP for use in food or feed.

It is an object of the present invention to address these problems in the production of single cell protein.

SUMMARY OF THE INVENTION

The present invention seeks to provide a process for producing SCP. The process preferably comprising the steps of: a) growing a thermophilic fungus in a medium containing a fermentable carbon-rich feedstock; wherein the fungus is grown in submerged culture under non-sterile conditions at a temperature higher than 45° C. and a pH of less than 3.8; and, b) recovery of SCP from the medium in the form of biomass of the thermophilic fungus grown in step a). Preferably in the process the concentration of the carbon-rich feedstock is below a concentration at which toxic compounds in the feedstock reduce the growth rate of the fungus, and/or the carbon-rich feedstock is fed to the medium at a rate at which the concentration of the carbon-rich feedstock is kept below the concentration at which toxic compounds in the feedstock reduce the growth rate of the fungus. It is understood that the concentration at which toxic compounds in the feedstock do not reduce the growth rate of the fungus is defined and/or determined as the highest concentration of the carbon-rich feedstock which does not cause a reduction in at least one of the rate of $CO_2$ production and the rate of $O_2$ consumption by the fungus. Therefore, preferably in a process of the invention, the carbon-rich feedstock in the medium is at a concentration, or is fed to the medium at a rate to maintain a concentration of less than 5, 4, 3 or 2% (w/v) dry matter.

In one embodiment, the process according to the invention, is a process comprising the use of two or more fermenters, wherein at least a first fermenter is emptied for harvesting and optionally cleaning, while in at least a second fermenter growth of the fungus continues, wherein preferably after harvesting and optional cleaning the empty first fermenter is filled with at least part of the content of the second fermenter wherein growth continued during harvesting and optional cleaning of the first fermenter.

A preferred process of the invention is a fed-batch process, a repeated fed-batch process or a continuous process, which further preferably is a carbon-limited process, or at least a process that is not nitrogen-limited.

The fungus that is grown in a process according to invention, preferably is a thermophilic fungus that is a strain of a fungal genus selected from the group consisting of *Rasamsonia, Talaromyces, Penicillium, Acremonium, Humicola, Paecilomyces, Chaetomium, Rhizomucor, Thermomyces, Rhizopus, Myceliophthora, Thermoascus, Thielavia, Thermomucor, Mucor, Stibella, Melanocarpus, Malbranchea, Dactylomyces, Canariomyces, Scytalidium, Myriococcum, Corynascus*, and *Coonemeria*. More preferably, the thermophilic fungus is a strain of a fungal species selected from the group consisting of *Rasamsonia composticola Rasamsonia emersonii, Talaromyces emersonii, Rhizomucor miehei, Rhizomucor pusillus, Thermomucor indica-seudaticae, Thielavia terricola, Thielavia terrestris, Thermoascus thermophilus* and a *Rhizopus* sp. of which the strains *Rasamsonia composticola* strain CBS 141695, *Rasamsonia emersonii* CBS 143030, *Thermomucor indicae-seudaticae* CBS 143027 and CBS 104.75, *Rhizomucor miehei* CBS 143029, *Rhizomucor pusillus* CBS 143028, *Thermoascus thermophilus* CBS 528.71, *Thielavia terrestris* CBS 546.86, *Talaromyces emersonii* CBS 393.64 and *Thermothelomyces thermophila* CBS 117.65 and *Rhizopus* sp. CBS 143160. are more preferred, of which strains CBS 141695, CBS 143030, CBS 143027, CBS 143029, CBS 143160 and CBS 143028 are most preferred.

In a preferred process of the invention, e.g. if applied in animal feed the fermentable carbon-rich feedstock is one or more of a by-product or waste from agriculture or food production, silage and an organic fraction of municipal solid waste (MSW). Preferably, the fermentable carbon-rich feedstock is one or more of sugar beet pulp, liquid C-starch from grain processing, vegetable waste from production of peeled, cut vegetables or rejected vegetables, Palm mill residues, including palm oil mill effluent (POME), and empty fruit bunches (EFB) and palm fronds. For the production of SCP for the manufacture of food products one can also use corn, potato, wheat, rice, cassava, sugar cane or sugar can juice, sugar beet or sugar beet juice or thick juice, glucose syrups, of any other vegetable product suitable for food application.

It is further preferred in a process according to the invention that the medium contains and/or is fed a nitrogen source. Preferably, the nitrogen source comprises one or more of ammonia, urea and nitrate. More preferably, the nitrogen source is one or more of amines present in burden condensates obtained from evaporation of molasses, sugar beet or cane vinasses, vinasses from wine industry, grape residues, potato protein liquor (PPL), Corn steep liquor (CSL), ammonia from animal farm exhaust gas cleaning scrubbers, and the thin fraction of manure processing.

In a process according to the invention, the biomass is preferably recovered from the medium by at least one of sieving, filtration and decantation, whereby preferably the dry matter concentration of the filtered or devastated biomass (cake) is at least 12, 15, 20, 25, 30, 35, 40, 45%, 50% (w/v). Preferably, the biomass is recovered from the medium by at least one of rotating drum filtration, a filter press, a belt filter, a sieve or DSM screen, rotating sieve, belt press and a decanter centrifuge, and whereby more preferably, the biomass cake can e.g. be further dried by pressing residual water out.

In a preferred process according to the invention, the water fraction that is obtained after sieving, filtering, decanting and/or further pressing the biomass (cake) is recycled back to the fermentation and/or used for further fermentation batches. In a further preferred process of the invention the fermenter is operated without any cooling device that requires input energy.

In one aspect, the invention relates to a thermophilic fungal strain. Preferably, the fungal strain is selected from the group consisting of the strains *Rasamsonia composticola* strain CBS 141695, *Rasamsonia emersonii* CBS 143030, *Thermomucor indicae-seudaticae* CBS 143027, *Rhizomucor miehei* CBS 143029, *Rhizomucor pusillus* CBS 143028 and *Rhizopus* sp. CBS143160.

In another aspect, the invention relates to an SCP product. The SCP product preferably comprises protein from biomass of at least one thermophilic fungal strain selected from the group consisting of the strains *Rasamsonia composticola* strain CBS 141695, *Rasamsonia emersonii* CBS 143030, *Thermomucor indicae-seudaticae* CBS 143027 and CBS 104.75, *Rhizomucor miehei* CBS 143029, *Rhizomucor pusillus* CBS 143028, *Thermoascus thermophilus* CBS 528.71, *Thielavia terrestris* CBS 546.86, *Talaromyces emersonii* CBS 393.64 and *Thermothelomyces thermophila* CBS 117.65 and *Rhizopus* sp. CBS143160, of which strains CBS 141695, CBS 143030, CBS 143027, CBS 143029 and CBS 143028 and CBS 143160 are preferred. Preferably the protein in the biomass has a sum of total essential amino acids that is at least 10% higher than the sum of total essential amino acids in soybean protein, and wherein more preferably the protein in the biomass has at least one of a lysine contents of at least 8.5% of total amino acids and a phenylalanine contents of at least 10% of total amino acids.

In a further aspect the invention relates to a food or feed product comprising protein from biomass of at least one thermophilic fungal strain selected from the group consisting of the strains *Rasamsonia composticola* strain CBS 141695, *Rasamsonia emersonii* CBS 143030, *Thermomucor indicae-seudaticae* CBS 143027 and CBS 104.75, *Rhizomucor miehei* CBS 143029, *Rhizomucor pusillus* CBS 143028, *Thermoascus thermophilus* CBS 528.71, *Thielavia terrestris* CBS 546.86, *Talaromyces emersonii* CBS 393.64, *Ther-*

*mothelomyces thermophila* CBS 117.65 and *Rhizopus* sp. CBS 143160 of which strains CBS 141695, CBS 143030, CBS 143027, CBS 143029 and CBS 143028 and CBS 143160 are preferred.

SHORT DESCRIPTION OF DRAWINGS

The present invention will be discussed in more detail below, with reference to the attached drawings.

FIG. 1 describes a total process outline for a process according to the invention wherein sugar beet pulp is used as fermentable carbon-rich feedstock for growing a thermophilic fungus for the production of single cell protein (BETUFEED) and a preparation fungal hydrolytic enzymes (BETUZYM) and a stream of liquid sugar beet pulp, which can be sold directly to animal feed clients or industrial use, but it can also fed to the fermenter dependent on market demands.

DESCRIPTION OF EMBODIMENTS

The present invention relates to the production of single cell protein. In particular, the invention relates to a process for producing single cell protein wherein a biomass of a thermophilic fungus is produced as single cell protein.

The term "single cell protein" will be abbreviated "SCP" and is herein understood to refers to biomass consisting essentially of cells of organisms that exist in unicellular, or single cell, state, including unicellular bacteria, yeasts, fungi or algae, and which biomass, preferably in dried form, is suitable as dietary source of protein or protein supplement in human food or animal feed.

In this invention, a novel process concept was developed, which uses process conditions such as a high temperature and low pH, and a thermophilic fungus that produces its own extracellular hydrolytic enzymes, which allow the process to be run under non-sterile conditions because at temperature higher than 45° C. and a pH of less than 3.8 other (micro) organisms will not be able to invade and/or compete with the fungus. Therefore, preferably a thermophilic fungus is used that can grow on energy-rich carbon-dominated feedstocks including both simple sugars such as sucrose and glucose, fructose, as well as polymeric sugars such as starch, inuline, cellulose, hemicellulose, chitin, pectin as well as organic acids such as lactic acid, acetic acid, formic acid, and ethanol and methanol (these metabolites are often formed in silage processes or from splitting them off from pectin and hemicellulose), as well as lipids present in the form of a triglyceride or phospholipids. Also the conversion of other sugars such as those present in hemicellulose; rhamnose, fucose, galactose, xylose arabinose, mannose, galacturonic acid, glucuronic acid etc. is needed as well as raffinose, melibiose, stachyose etc. is preferred to enhance the protein product of the feed ingredient and minimizing carbon burden from the filtrate which has to go to the waste water treatment/biogas installation. Also the conversion of betaine, ferulic acid and coumaric acid by the fungus is preferred to maximize yield. The advantage of the many thermophilic fungi that occur in processes like composting is that they can stand very harsh conditions and can produce the enzymes to split the polymeric substrates such as carbohydrates into monomeric sugars and convert them.

In a first aspect, the invention relates to a process for producing SCP. The process preferably process comprises the step of: a) growing a thermophilic fungus in a medium containing a fermentable carbon-rich feedstock. Preferably, in step a) the fungus is grown in submerged culture. Preferably, in step a) the fungus is grown under non-sterile conditions. Preferably, in step a) the fungus is grown at a temperature of 46, 47, 48, 49, 50, 51, 52, 53, 54 or 55° C. or more. Preferably, in step a) the fungus is and at a pH of 3.8, 3.75, 3.74, 3.73, 3.72, 3.71, 3.7, 3.6, 3.5, 3.4, 3.3, 3.2, 3.1 or 3.0 or less. The process preferably comprises a further step of b) recovery of SCP from the medium in the form of biomass of the thermophilic fungus grown in step a).

One problem to be solved in the production of SCP at low pH is the toxicity of many fermentable carbon-rich feedstocks. Particularly hydrolysed biomass or silage products are likely to contain compounds that are toxic to most microorganism, including e.g. organic acids such as acetic acid, lactic acid, ferulic acid, coumaric acid, formic acid. These acids are especially toxic at low pH, when they are in non-dissociated form and as such can readily penetrate the cell wall and acidify the cell's interior. When such fermentable carbon-rich feedstocks are applied in fermentations at low pH and at a dry matter concentration (w/v) that is higher than 2, 5 or 10%, the toxicity will be prohibitive for fungal growth.

Therefore, preferably in a process of the invention, in step a), the concentration of the carbon-rich feedstock is at a level at which toxic compounds in the feedstock do not reduce the growth rate of the fungus. More preferably, the carbon-rich feedstock is fed to the medium at a rate at which at which toxic compounds in the feedstock do not reduce the growth rate of the fungus. For example, in a process according to the invention, the carbon-rich feedstock in the medium is at a concentration, or is fed to the medium at a rate to maintain a concentration, of less than 5, 4, 3 or 2% (w/v) dry matter. The fermentability of a feedstock can conveniently be checked or monitored by measuring at least one of the $CO_2$ content and the $O_2$ content of the exhaust gas of the fermenter. The maximum concentration at which a feedstock can be used without negatively affecting the growth rate of the fungus can thus be determined by increasing concentration if the feedstock in the medium until a concentration is reached at which at least one of rate of $CO_2$ production and the rate of oxygen consumption decreases. Preferably therefore, in a process of to the invention, the concentration at which toxic compounds in the feedstock do not reduce the growth rate of the fungus is determined and/or defined as the highest concentration of the carbon-rich feedstock which does not cause a reduction in at least one of the rate of $CO_2$ production and the rate of $O_2$ consumption by the fungus. A well fermenting feedstock will allow a rapid increase of the rate of $CO_2$ production or oxygen consumption as may be determined by resp. an increase in $CO_2$ concentration or a decrease in the oxygen concentration in the off gas from the fermentation. When $CO_2$ evolution rate is low, growth is slow and can be enhanced by diluting with water until growth starts taking off and $CO_2$ production accelerates.

In the Examples we have e.g. applied a fed-batch technique by diluting the hydrolysed biomass to <2% dry matter before inoculation, let the batch phase complete and when organic acids and sugars are consumed, start a feed with hydrolysed biomass at a slow rate at glucose limiting conditions (e.g. glucose=<2 g/L) to allow the fungus to consume all the toxic organic acids fed to the fermenter.

A preferred process of the invention is therefore a fed-batch process, a repeated fed-batch process (wherein repeatedly a part of the fermentation broth is harvested) or a continuous process. Preferably in such processes, the dilution rate, i.e. the rate at which the feedstock is fed into the fermenter, should be as high as possible but preferably not higher than the maximum specific growth rate of the fungus to prevent washing out of the fungus. In the processes of the invention, the dilution rate preferably is in the range of 0.05 to 0.2 1/hr, which refers to a residence time in the fermenter of 5 to 20 hours in the fermenter. The dilution rate thus preferably is at least 0.05 or 0.1 1/hr and preferably not higher than 0.2 1/hr.

In a further preferred process of the invention the process comprises the use of two or more fermenters, wherein at least a first fermenter is emptied for harvesting and optionally cleaning, while in at least a second fermenter growth of the fungus continues. Cleaning of the empty fermenter preferably comprises disinfection, e.g. by rinsing with acid (such as sulfuric acid or phosphoric acid), alkaline (such as NaOH or KOH), disinfectants (such as hydrogen peroxide or peracetic acid) or heat (e.g. steam), so as to control infection of the fermentation by e.g. bacteria or yeasts. Cleaning is preferably performed using a CIP installation. In one embodiment the process is run in at least one pair of fermenters, which are alternatingly emptied for harvesting and optional cleaning once per 1, 2 or 3 days. This operation is an improved version of the process that allows non-sterile conditions to be practised without instability of the process or deviations in quality or process stability. In a further preferred embodiment of the process, after harvesting and optional cleaning, the empty first fermenter is filled with at least part of the content of the second fermenter wherein growth continued during harvesting and optional cleaning of the first fermenter. In a next round of the process, the second fermenter is harvested and optionally cleaned, and then filled with at least part of the content of the first fermenter wherein growth continued during harvesting and optional cleaning of the second fermenter, and so on. In yet another embodiment of the process, the harvested fermentation batches are collected in a further continuous fermentation phase to allow higher product yields and/or stable feeding of the DSP area.

It is preferred in the processes of the invention that, the dry matter concentration (of the feedstock) is managed such that the oxygen consumption rate does not exceed the oxygen transfer capacity of the fermenter, which would lead to insufficient aeration and incomplete substrate oxidation.

In the processes of the invention, the dry matter concentration of the feedstock in the medium is further preferably optimized such that down-stream processing is most cost-efficient. To minimize the amount of harvested fermented medium to be filtered and/or decanted and to minimize the amount of water to be evaporated (e.g. water coming from the filtrate in case of selling a mineral fertilizer), the dry matter concentration of the feedstock in the medium preferably is as high as possible. On the other hand, when the dry matter concentration of the feedstock in the medium is too high, the viscosity of the fungal broth will increase and the oxygen transfer will become problematic. The inventors have found that the optimal dry matter concentration of the feedstock in the medium in the fermenter is in the range of 2-15% dry matter (w/v), depending on the raw materials used, salt stress, toxic metabolites. In addition the rheology of broth partly determined by the growth morphology of the fungus. The preferred growth morphology of the fungus in processes of the invention is a hyphal length that is short enough to give a low viscosity of the broth to allow easy oxygen transfer and mixing, but long enough to allow easy filtration or decantation at low g-values. Preferably therefore the hyphal length is in the range of 10-500 µm (micrometre) and preferably the hyphae are not too heavily branched. More preferably, the hyphal length is in the range of 30-300 µm. The mycelium preferably can be easily harvested by retention on a sieve or a screen, preferably with 0.1, 0.5, 1 or 2 mm diameter of pores.

It is further preferred in the processes of the invention that nitrogen limitation is avoided. The fungus is therefore preferably grown under carbon-limitation. Thereby the protein content of the biomass produced can be maximised and accumulation of carbon reserve and/or storage compounds, such as e.g. trehalose, glycogen and/or lipids, as a result of carbon excess can be avoided.

The fungus that is used in the process of the invention, i.e. the fungus that is grown in the process, preferably is a thermophilic fungus. A thermophilic fungus for use in the invention preferably is a fungus that grows at a temperature of at least 45, 46, 47, 48, 50, 51, 52, or 55° C., sometimes even higher than 56° C. A thermophilic fungus for use in the invention preferably is also a fungus that grows at low, i.e. acidic pH. A preferred thermophilic fungus grows at a pH of 3.8, 3.75, 3.74, 3.73, 3.72, 3.71, 3.6, 3.5, 3.4, 3.3, 3.2, 3.1 or 3.0 or less. A thermophilic fungus for use in the invention preferably is a cellulolytic and/or hemi-cellulolytic fungus.

"Fungi" are herein defined as eukaryotic microorganisms and include all species of the subdivision Eumycotina (Alexopoulos et al., 1962, In: Introductory Mycology, John Wiley & Sons, Inc., New York). The term fungus thus includes both filamentous fungi and yeast. "Filamentous fungi" are herein defined as eukaryotic microorganisms that include all filamentous forms of the subdivision Eumycotina and Oomycota (as defined by Hawksworth et al., 1983, In: Ainsworth and Brisby's Dictionary of the Fungi. 7th ed. Commonwealth Mycological Institute, Kew, Surrey). The filamentous fungi are characterized by a mycelial wall composed of chitin, cellulose, glucan, chitosan, mannan, and other complex polysaccharides. Vegetative growth is by hyphal elongation and carbon catabolism is obligately aerobic.

A thermophilic fungus for use in the invention preferably is filamentous fungus. A preferred thermophilic fungus for use in the invention is a strain of a fungal genus selected from the group consisting of *Rasamsonia, Talaromyces, Penicillium, Acremonium, Humicola, Paecilomyces, Chaetomium, Rhizomucor, Rhizopus, Thermomyces, Myceliophthora, Thermoascus, Thielavia, Mucor, Stibella, Melanocarpus, Malbranchea, Dactylomyces, Canariomyces, Scytalidium, Myriococcum, Corynascus,* and *Coonemeria*. More preferably, the thermophilic fungus is a strain of a fungal species selected from the group consisting of *Rasamsonia composticola, Talaromyces emersonii, Rasamsonia emersonii, Thermomucor indicae-seudaticae, Rhizomucor miehei, Rhizomucor pusillus, Thielavia terricola* var *minor,* a *Rhizopus* sp. and *Thermoascus thermophilus*. Suitable strains of these thermophilic fungi can e.g. be isolated from Dutch compost and have been successfully used by the inventors to demonstrate that these thermophilic fungi grow well on complex nutrients at high temperature and low pH. Next to this, many thermophylic strains for use in the invention such as *Thielavia terricola* var *minor* and *Thermoascus thermophilus*, which also grow well at high temperature and low pH. A *Rhizopus* sp. can be any one of *Rhizopus oryzae, Rhizopus chlamydosporus, Rhizopus microsporus, Rhizopus stolonifer* or *Mucor indicus*. Alternatively, a *Rhizopus* sp. can be a yet unidentified *Rhizopus* or *Mucor* species that corresponds with *Rhizopus* sp. CBS 143160. Preferably the *Rhizopus* sp. is safe for use in food, more preferably the *Rhizopus* sp. is a tempeh starter.

Preferred strains of the above-mentioned thermophilic fungi for use in the invention include the following strains that were deposited under the regulations of the Budapest Treaty at the Westerdijk Fungal Biodiversity Institute, Uppsalalaan 8, P.O. Box 85167, 3508 AD, Utrecht, The Netherlands (formerly referred to as Centraalbureau voor Schimmelcultures, CBS) at the dates indicated and assigned the accession numbers as indicated: *Rasamsonia composticola* CBS 141695 (Jul. 29, 2016), *Thermomucor indicae-seudaticae* CBS 143027 (Jul. 21, 2017), *Rhizomucor miehei* CBS 143029 (Jul. 21, 2017), *Rhizomucor pusillus* CBS 143028 (Jul. 21, 2017), *Rasamsonia emersonii* strain CBS 143030 (Jul. 30, 2017) and *Rhizopus* sp. CBS 143160 (Aug. 11, 2017). Further preferred strains for use in the invention include *Thermomucor indicae-seudaticae* CBS 104.75, *Thermoascus thermophilus* CBS 528.71, *Thielavia terrestris* CBS 546.86, *Talaromyces emersonii* CBS 393.64 and *Thermothelomyces thermophila* CBS 117.65. Particularly preferred for use in the invention are the strains *Rasamsonia composticola* strain CBS 141695, *Rasamsonia emersonii* CBS 143030, *Thermomucor indicae-seudaticae* CBS 143027, *Rhizomucor miehei* CBS 143029, *Rhizopus* sp. CBS 143160 and *Rhizomucor pusillus* CBS 143028.

A thermophilic fungus for use in the invention further preferably is a fungus from which is biomass can be obtained with a high protein content. Preferably the protein content of the biomass is at least 30, 35, 40, 45, 50 or 55% (w/v) on dry matter basis. The high protein strains most likely have a lower content of carbon reserve and/or storage compounds, such as e.g. trehalose, glycogen and/or lipids A thermophilic fungus for use in the invention further preferably is a fungus of which the proteins in the biomass contain one or more of the essential amino acids. Preferably the proteins are rich in such essential amino acids. Essential amino acids are herein understood to include at least one or more of lysine, phenylalanine, threonine, methionine, valine, arginine, histidine, tryptophan, isoleucine and leucine, of which, lysine, threonine, methionine are most preferred.

As the SCP product is intended for use in food or feed for animals for human consumption, the production of mycotoxins, such as e.g. Ochratoxin A and Fumonisins, by the thermophilic fungus to be applied is undesirable. Therefore a thermophilic fungus for use in the invention preferably is selected that does not produce any mycotoxins. This screening is preferably done by genetic means, by verifying e.g. with PCR or with whole genome sequencing, the absence of the presence of genes in mycotoxin pathways, and in the case such genes are present, by verifying that, under process conditions used, these genes are not expressed and/or these toxic compounds are not produced.

Alternatively, a thermophilic fungi to be used in the processes of the invention is genetically modified to produce increased amounts of hydrolytic enzymes, preferably invertase (e.g. for *Rasamsonia*), cellulolytic and/or lignocellulolytic enzymes, are used in the present invention, such as e.g. described in WO2011/000949. The enhanced enzyme production can lead to reduced hydrolysis times, smaller tanks can then be used and the enzyme-containing filtrate/decantate can be commercialised as secondary product.

The fermentable carbon-rich feedstock that is used in the process of the invention can be any feedstock that can serve as carbon and energy source for the thermophilic fungus. Such carbon-rich feedstock can be crops freshly harvested from the primary production of food sugars such as corn, sugar beet, thin juice, thick juice, sugar cane juice. However, particularly when the SCP is intended to be applied in animal feed, it is more logical and preferred to use as feedstock carbon-rich side- or by-products or waste streams from agriculture and/or food production, such as e.g. sugar beet pulp, liquid C-starch from grain processing, vegetable waste from production of pealed or cut vegetables or from rejected vegetables, such as e.g. peels from potato peels and cutting residuals from French fries production, refused potato from trading, and also palm mill residues such as including palm oil mill effluent (POME) containing predominantly palm oil and palm oil fatty acids and empty fruit bunches (EFB) or palm fronds. Also one can think of feedstocks stored as a silage, so it can be processed into SCP year round, while the feedstock is harvested in a campaign such as in the case of sugar beet pulp or the leaves of potato or sugar beet. Also, silages from whole fodder beet can be used, e.g. combined with corn or whole corn or the ensilaged form of thereof, although the lignin rich corn stover is not preferred, neither sugar cane bagasse. Pentoses e.g. from lignocellulosic hydrolysates can also be used. These syrups contain mainly glucose, xylose, arabinose, mannose and galactose. Another gigantic source of raw material as fermentable carbon-rich feedstock for the processes of the invention is the organic fraction of municipal solid waste (MSW). Also sludge from anaerobic waste water can be used, e.g. including toilet paper. Also this process can eliminate the use of flocculants to dewater anaerobic sludge as the fungi in this process can be sieved and pressed without flocculants. This may become more important once collection practices have improved and clean enough organic streams can be harvested without further processing.

For the production of SCP for the manufacture of food products (for human consumption), any product of plant origin that is compatible with or acceptable for application in food can be applied in the invention as carbon-rich feedstock, including e.g. corn, potato, wheat, rice, cassava, sugar cane or sugar cane juice, sugar beet or sugar beet juice or thick juice, molasses, cane molasses, glucose syrups, fructose syrups, of any other vegetable product suitable for food application. A lipid rich fraction, e.g. vegetable oils or fractions therefrom, can also be applied in the invention as carbon-rich feedstock, as the selected organisms also consume triglycerides, including e.g. soybean oil or sunflower oil etc.

In the processes of the invention, the medium further preferably contains and/or is fed with a source of nitrogen. Preferably, the nitrogen source comprises one or more of (a source of) ammonia, urea and nitrate. More preferably, as a nitrogen source are the reduced form such as urea and ammonium. $NH_3$ or $H_2NO_3$ can additionally be to control pH in the fermenter or urea can be used as a pH-independent supply of nitrogen source. Also preferred are nitrogen sources from waste streams. These include e.g. one or more of amines present in burden condensates obtained from evaporation of molasses, sugar beet or cane vinasses, vinasses from wine industry, grape residues, potato protein liquor (PPL), Corn steep liquor (CSL), ammonia from animal farm exhaust gas cleaning scrubbers, and the thin fraction of manure processing.

In optional further step of b) of the process of the invention, the SCP is recovered from the medium in the form of biomass of the thermophilic fungus grown in step a). Preferably, the biomass is recovered from the medium by at least one of sieving, filtration and decantation. More preferably, the biomass is recovered from the medium by at least one of rotating drum filtration, a filter press, a belt filter, a decanter centrifuge and sieving. Preferably biomass is recovered by sieving on a sieve or a screen, with 0.1, 0.5, 1 or 2 mm diameter of pores. More preferably, the biomass is recovered by at least two, three or four consecutive rounds of sieving on a sieve or screen whereby a smaller diameter of pores is applied in each subsequent round of sieving. E.g. a first round of sieving using 2 mm pore diameter, followed by subsequent rounds of 1, 0.5 and/or 0.1 mm.

Preferably, dry matter concentration of the sieved, filtered or decantated biomass (cake) is at least 12%, 15%, 20%, 25%, 30%, 35%, 40%, 45%, 50%, 52%, 53% 54% or 55% (w/v). Optionally, dry matter concentration of the sieved, filtered or decantated biomass (cake) is further increased by further removal of water, i.e. drying.

The biomass cake can e.g. be further dried by pressing (more of) the residual water out using e.g. compressed air using a pneumapress and/or mechanical pressing, using e.g. a belt press or a screw press. In warmer climates the biomass (cake) can simply dried to the air (in the sun). After pressing the biomass to a cake, optionally the cake can be milled or extruded e.g. to enable drying, preferably air drying. Preferably, the particle size of the pressed mycelial biomass cake is reduced by physical means to enable (more efficient) drying of the pressed cake. This can optionally done by extrusion of the mycelial cake through holes with a diameter of 0.6, 0.7, 0.8, 0.9, 1.0, 1.2, 1.4, 1.6, 1.8 or 2 mm, using extruders that are known in the art per se. If however the dry matter concentration of the pressed cake after pressing is so high, that extrusion of the pressed cake is no longer possible (e.g. when the cake is too firm to allow for extrusion), the particle size of the cake can be reduced by a combination of milling and sieving. As a milling step any type of mill known in the art per se can be used, such as e.g. a knife mill or a hammer mill, etc. To obtain homogeneous particle size of the milled pressed cake, the larger particles still present after milling can be removed before drying by sieving with a pore diameter size in the sieve of 0.5, 1.0, 1.2, 1.4, 1.6, 1.8, 2.0, 2.5 or 3 mm. The resulting milled cake would have preferably a particle size between 1-3 mm before drying. By reducing the particle size, evaporation of water from the pressed cake is more efficient and faster.

Preferably drying of the cake is done by using waste heat, e.g. from a plant where hot water is obtained after condensation of gas (e.g. ethanol distillation, potato cooking, steam-pealing of potatoes, etc.). The air can be heated using a heat exchanger to heat up dry air with hot water from the heat source.

Drying of the extruded or milled cake is preferably done at temperatures of 30-70° C. The hot air can then dry the cake in a gentle and cost effective way in a belt dryer or fluid bed dryer. Steam drying at high temperatures (e.g. >80° C.) is not preferably avoided as it can negatively influence digestibility of the proteins d by denaturing and baking and even chemical decomposition of the amino acids by Maillard reactions.

The thermophilic fungus to be applied in the process of the invention therefore preferably has good filtration properties (see above) so that a protein rich animal feed cake can be obtained by simple filtration such as rotating drum filtration, screen strap, filter press, belt filter etc. or a decanter centrifuge operated at low g forces (Suman et al., 2015 supra), a sieve, a DSM screen, belt sieve, belt press, screw press. The moist product can be stabilized by adding organic acids such as formic acid, acetic acid, benzoic acid to prevent microbial deterioration, optionally combined, by keeping the pH<4.5. Although cost of production of liquid feeds is generally lower, optional drying of the animal feed cake using e.g. fluid bed drying, drum drying, belt drying or any other means of drying can be considered if transport, logistics and/or storage stability demand so. In a particularly preferred process the concentration of the biomass is done in multiple steps and combinations: e.g. by subsequently sieving through pore sizes selected from at least two of 2 mm, 1 mm, 0.1 mm and 50 um; then concentrating by at least one of a screen strap, pressing using screw press, a belt press and a pneumapress. In a most preferred process for concentrating the biomass can simply be the combination of a DSM screen (with optimized diameter screen), a screen strap and a belt press.

In one embodiment of the process of the invention, the filtrate containing water and enzymes produced by the fungus can be recycled and used in a next fermentation round. Preferably, water utilisation in the overall process is minimised. Preferably therefore in the process, the water fraction (filtrate) that is obtained after sieving, filtering, decanting and/or further pressing the biomass (cake) is recycled back to the fermentation and/or (re-)used for further fermentation batches. This is particularly preferred when the fermentation is run at low dry matter (e.g. less than 10, 5, or 2% dry matter). Preferably at least 10, 20, 50, 60, 70, 80, 90 or 95% of the filtrate from the recovery process is recycled. If as a result of recycling salts and non-consumables accumulate in too high concentrations, part of the filtrate may be bled to the waste water treatment and/or used for fertilizer production. Preferably therefore, the titrants in the process are chosen such that a suitable fertilizer composition may be obtained from the filtrate, preferably a composition comprising one or more of N, P, K, S, Mg and Ca. Recycling of the water fraction will improve the overall economics of the process by reducing waste water treatment capacity and/or fresh water usage. Optionally, the filtrate of a first fermentation can be used in a second fermentation that allows a second organism to consume the carbon source that is not consumable by the first organism. Also application of two or more organisms in one fermentation would be possible. The application of two different thermophilic fungi, either simultaneously or subsequently in two or more fermentation runs, would allow optimization of yield, amino acid profile, taste, physical behaviour and many more. In a preferred embodiment, the filtrate obtained from a first fermentation with one or more strains of thermophilic fungi is used in a second fermentation with one or more strains of thermophilic fungi whereby at least one thermophilic fungal strain in the second fermentation differs from the strains used in the first fermentation. Preferably, the strains for the first and second fermentations are chosen to be complementary in terms of amino acid profiles of their biomass and/or capability to consume fractions of the carbon-rich feedstock. Preferably, the strains of thermophilic fungi that are used in the first and second, and optionally further fermentations, are selected from the thermophilic fungi and strains mentioned hereinabove. An example of two complementary thermophilic fungi that may be used subsequently are e.g. a strain of *Thermomucor* and a strain of *Rasamsonia*, as e.g. exemplified in Example 11 herein.

Alternatively, the enzymes can be recovered and sold as enzyme preparation for use in animal feed or detergent washing, industrial cleaning etc.

Another advantage of the use of thermophilic fungi is that a fermenter can be operated without any cooling (Suman et al., 2015 supra), e.g. without any (active) cooling device that requires an input of energy. Thus, neither an internal cooling coil in the fermenter nor cooling coil in baffles of a stirred fermenter, nor in fermenter wall, neither Riesel cooling is required, neither a cooling tower. An external cooling loop using a heat exchanger is not needed either. This will reduce the investment in the plant as the cooling relies only on evaporation of water and which will leave the fermenter via the exhaust gas exhaust of the fermenter via which the $CO_2$ is ventilated and/or heat that passively exchanged with the fermenter's environment.

Preferably, the fermenter has a means for introducing sterile air (to prevent foreign fungal spores or yeasts to invade) and, preferably a means to control pH with e.g. $NH_3$ and/or or $H_2SO_4$ or $H_2NO_3$. In some instances also a need for phosphate might be apparent and in such cases the use of ammonium phosphate is preferred in the processes of the invention.

The fermenter in which the processes of the invention are run can be in principle be any type of fermenter known in the art. Advantageously the fermenter is a simple bubble column, which can be operated at very large scale such as e.g. >100 m³, >200 m³, >500 m³, >1000 m³, >2000 m³ or >3000 m³, thereby reducing the number of fermenters per factory, the total investment and operational cost.

The SCP obtained in a process according to the invention can e.g. be used to supplement feed for a variety of different livestock animal types, including pigs, poultry, ruminant livestock as well as aquatic fish and crustacean species. For the application of the SCP as fish feed, preferably the feed is enriched with a source of omega-fatty acids fatty acids such as fish oil, or a lipid rich algae, such as *Cryptocodinium cohnii*, or *Traustochytrium aureum*. An additional advantage of the SCP obtained in a process according to the invention is that the acidic pH at which the SCP is produced will prevent contamination of the SCP by problematic bacteria such as *E. coli, Salmonella, Bacillus cereus*, Enterobacteriaceae, *Listeria* etc., which may be present in SCP produced in other processes.

Alternatively, the SCP obtained in a process according to the invention can be used as a food or food ingredient.

Whereas e.g. soybean has a lysine content of appr. 6% of total amino acids, existing fungal SCPs have lysine contents of total amino acids of 8.3% for *Fusarium venenatum* biomass (Quorn™) or 5.6% for Pekilo protein (*Paecilomyces varioti*). The inventors here have now found that the sum of total essential amino acids of *Rasamsonia composticola* proteins appeared to be 16% higher than that of soybean protein and for *Thermomucor indicae-seudatica* even 25% higher than that of soybean protein. Furthermore, the inventors have found that SCP from *Thermomucor indicae-seudatica* (e.g. strain CBS 143027) has a lysine content of more than 8.5% and even more than 10% of total amino acids and a phenylalanine contents of at least 10% of total amino acids. SCP from *Thermomucor* strains thus not only has a high protein content but also a high lysine and phenylalanine content. *Thermomucor* SCP thus has a surprisingly high nutritional value.

In one aspect therefore the invention relates to a thermophilic fungal strain as isolated by the inventors. Preferably, the thermophilic fungal strain is selected from the group consisting of the strains *Rasamsonia composticola* strain CBS 141695, *Rasamsonia emersonii* CBS 143030, *Thermomucor indicae-seudaticae* CBS 143027, *Rhizomucor miehei* CBS 143029, *Rhizopus* sp. CBS 143160 and *Rhizomucor pusillus* CBS 143028.

In a further aspect the invention relates to an SCP product comprising protein from biomass obtainable or produced in a process as herein described above. Preferably, the SCP product comprises or consists of dried biomass with a dry matter concentration of at least 25%, 30%, 35%, 40%, 45%, 50%, 52%, 53% 54% or 55% (w/v) and which is milled or extruded to an average particle size in the range of 1-3 mm. With this the product can be conveyed to pack it, convey it to a next processing step. The protein rich product can then subsequently be dried.

Preferably, an SCP product according to the invention comprises protein from biomass of at least one thermophilic fungal strain selected from the group consisting of the strains *Rasamsonia composticola* strain CBS 141695, *Rasamsonia emersonii* CBS 143030, *Thermomucor indicae-seudaticae* CBS 143027 and CBS 104.75, *Rhizomucor miehei* CBS 143029, *Rhizomucor pusillus* CBS 143028, *Thermoascus thermophilus* CBS 528.71, *Thielavia terrestris* CBS 546.86, *Talaromyces emersonii* CBS 393.64, *Thermothelomyces thermophila* CBS 117.65 and *Rhizopus* sp. CBS 143160, of which strains CBS 141695, CBS 143030, CBS 143027, CBS 143029, CBS 143160 and CBS 143028 are preferred. The SCP product can thus be biomass or biomass cake, recovered, pressed, dried, milled and/or extruded as described hereinabove. Preferably, the SCP product (or the protein in the biomass) has a sum of total essential amino acids that is at least 10% higher than the sum of total essential amino acids in soybean protein. More preferably, the SCP product (or the protein in the biomass) has at least one of a lysine contents of at least 8.5% of total amino acids and a phenylalanine contents of at least 10% of total amino acids.

In a further aspect the invention relates to a food or feed product comprising protein from biomass of at least one thermophilic fungal strain selected from the group consisting of the strains *Rasamsonia composticola* strain CBS 141695, *Rasamsonia emersonii* CBS 143030, *Thermomucor indicae-seudaticae* CBS 143027 and CBS 104.75, *Rhizomucor miehei* CBS 143029, *Rhizomucor pusillus* CBS 143028, *Thermoascus thermophilus* CBS 528.71, *Thielavia terrestris* CBS 546.86, *Talaromyces emersonii* CBS 393.64, *Rhizopus* sp. CBS 143160 and *Thermothelomyces thermophila* CBS 117.65, of which strains CBS 141695, CBS 143030, CBS 143027, CBS 143029, CBS 143160 and CBS 143028 are preferred.

Unless indicated otherwise all percentages dry matter are indicated as percentage weight per volume.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The present invention has been described above with reference to a number of exemplary embodiments as shown in the drawings and set forth in the examples below. Modifications and alternative implementations of some parts or elements are possible, and are included in the scope of protection as defined in the appended claims.

EXAMPLES

Example 1. Production of Protein Rich Animal Feed from Sugar Beet Pulp 1 ml of frozen mycelium of *Rasamsonia composticola* CBS 141695 (−80° C., glycerol stock) was thawed and inoculated to 35 ml of a yeast extract/glucose medium (20 g/L each) at pH 4.5 in baffled aerobic Erlenmeyer flasks of 250 ml sterilized 20 minutes at 121° C. and incubated at 220 rpm 25 mm throw at 45° C. for 48 hours.

10 ml of this 48 hr preculture was transferred to the following sugar beet pulp medium:

250 ml medium was prepared in a 2 L baffled Erlenmeyer flask containing a mineral solution containing sufficient K, P, S, Ca, Mg, Zn, Fe, Mn, Cu for good fungal growth (US20020039758), 1.75 gr/L NaNO$_3$, 1.75 gr/L di-ammoniumsulfate, 0.1 gr/L yeast extract and 20 gr/L Fibrex 500 (a commercial sugar beet pulp milled to fine mash Nordic Sugar). The medium was supplemented with 10 drops of soybean oil to prevent foaming and sterilized 20 minutes at 121° C.

After fermentation, the fermented mash was filtered over a Whatman filter and the cake was then dried to sample FSBP-1 (Fermented Sugar Beet Pulp) by freeze drying prior to analysis. Whereas sugar beet pulp has 10-11% protein on dry matter basis, the fermented sugar beet pulp sample FSBP-1 had a protein content of 230 g crude protein (N*6.25) per g dry matter and the following amino acid profile as given in Table 1.

TABLE 1

Amino acid profile in fermented Sugar beet pulp compared to Sugar beet pulp (Serena et al. Animal Feed Science and Technology 139 (2007) 109-124.

|  | Sugar beet pulp % | FSBP-1 % |
|---|---|---|
| Essential | | |
| Arginine | 6.2 | 5.7 |
| Histidine | 5.0 | 3.2 |
| Isoleucine | 5.9 | 5.8 |
| Leucine | 8.9 | 9.8 |
| Lysine | 10.6 | 6.6 |
| Methionine | 2.6 | 2.1 |
| Phenylalanine | 5.3 | 5.9 |
| Threonine | 6.7 | 6.6 |
| Valine | 9.1 | 8.1 |
| Non Essential | | |
| Alanine | 6.8 | 7.0 |
| Aspartic acid | 10.6 | 10.9 |
| Cysteine | 1.9 | 1.7 |
| Glutamic acid | 13.2 | 13.1 |
| Glycine | 6.2 | 6.1 |
| Ornithine | 0.0 | 0.0 |
| Proline | 0.3 | 0.0 |
| Serine | 0.2 | 7.2 |
| Tyrosine | 0.5 | 0.0 |

Example 2. Production of SCP in a Fed Batch Process

Sugar beet pulp was liquefied at 45° C. using 0.02 g Visco Reductase AC100 (Weiss Biotech) per gram sugar pulp from a silage process at 27% dry matter. The sugar beet pulp was diluted with water to a dry matter concentration of 8% and was shaken at 150 RPM 25 mm throw in shaker incubator. The pH of the silage was 3.8 at the start of the liquefaction, and after 3 hours the liquefied sugar beet pulp was added to a hydrolysis reactor, diluted with water to 5.2% dry matter and was stirred at 400 rpm in a 15 L stirred tank reactor and temperature was put at 60 C for another 6 hours, while pH was controlled at pH 4 using 8% ammonia as titrant. Then the hydrolysate was harvested and frozen until use as feed to a fermentation.

1 ml frozen vial (glycerol stock at −80° C.) of strain *Rasamsonia composticola* CBS 141695 was thawed and added to 35 ml medium in a 250 ml baffled shake flask containing yeast extract 20 g/L and glucose (20 g/L) medium at pH 4.5 sterilized at 121° C., 20 minutes. The culture was incubated at 45° C. for 24 hours and then transferred to a 250 ml medium of the same composition in a 2 L Erlenmeyer and grown for another 24 hours, 180 RPM 25 mm throw, 45° C.

In total 440 ml of such inoculum culture (2 flasks of 250 ml, lost some 100 ml water due to evaporation) were transferred to a 15 L fermenter with the following medium composition: 740 g Sugar Beet Pulp hydrolysate at 5.2% (as described above), 2 L tap water, 140 gram of a suitable mineral stock solution to provide enough phosphate, potassium, Magnesium, and trace elements), 14 gram di-ammonium sulphate. pH was set to 3.5 using sulphuric acid. And temperature was controlled at 45° C., while keeping oxygen high (>10%) using air sparging and increasing stirrer speed. After 21 hours a feed was started with the liquefied sugar beet pulp. 7.4 kg was added in 24 hours. The broth was then filtered over a Buchner funnel using Whatman 42 Cat No 1442090 filter paper at 250 mbar vacuum, and the broth could very easily be filtered at a flux of >300 L/m2/hr. The dry matter content of the biomass cake was 33% dry matter.

Fermentation of the hydrolysed sugar beet pulp (from ensilaged sugar beet storage) was not possible at 5% dry matter at pH 3.5 and 48° C. No start of fermentation was observed after 48 hrs due to toxic properties of acids at low pH.

Example 3. Production of Fish from Dried SCP 525 g of 33% dry matter biomass cake obtained from Example 2 was mixed with wheat gluten 12.4 gr, a commercial fish feed (27 gr) and 3.5 g calcium carbonate extruded through a 1 mm extruder and dried at 30° C. in a fluid bed dryer. 145 g dried SCP was obtained with appr. 30.8% protein on dry matter basis. 80% of all protein in this diet came from the SCP. The dried cake was milled and sieved over 0.5 mm sieve.

7 Tilapia fishes of in total 15.4 gram fresh weight were fed daily with this experimental feed after 30 days at 27-28 C, 58.7 g of fish was obtained while in total 109.5 g feed was added demonstrating that 0.54 g of fresh fish was obtained per gram feed. The fish were very lively and healthy, loved the food and had normal faeces.

Example 4. Production of Single Cell Protein from Potato Protein Liquid (PPL)

Potato protein liquor (PPL, 53% dry matter, 31.4% crude protein on dry matter, 15.1% potassium on dry matter) was obtained via Van der Stelt (EMSLAND factory).

1 ml of frozen mycelium of *Rasamsonia composticola* CBS 141695 (−80° C., glycerol stock) was thawed and inoculated to 35 ml of a yeast extract/glucose medium (20 g/L each) at pH 4.5 in baffled aerobic Erlenmeyer flasks of 250 ml sterilized 20 minutes at 121° C. and incubated at 220 rpm 25 mm throw at 45 C for 48 hours.

25 ml of this 48 hr preculture was transferred to the following growth medium:

250 ml medium was prepared in 2 L baffled aerobic Erlenmeyer flasks containing yeast extract/glucose medium (20 g/L each) at pH 4.5. The medium was supplemented with 10 drops of soybean oil to prevent foaming and sterilized 20 minutes at 121° C. Cultivation of the second stage inoculum phase was done at 180 RPM, 25 mm throw at 45° C.

250 ml of the very well grown culture was inoculated to a 15 L Cplus fermenter of Sartorius containing 3 L of water and 1.25 gr/L di-ammonium sulphate and PPL (as such, non-sterilized) was fed to the fermenter with a feed rate starting at 10 gr/hr at t=0 ramping up to 100 gr/hr at 10 hr, and keeping it there up to 15 hr, when 1000 g of PPL was fed. pH was controlled at 3.5+/−0.1 using 25% sulphuric acid as a titrant (PPL having a pH of 5.6). Temperature was controlled at 45° C., and aeration was done by 0.5 vvm aeration at 100 mbar overpressure and stirring at 750 rpm keeping oxygen at 40% or higher by adjusting the stirrer speed. The maximum specific growth rate of the organism based on the $CO_2$ evolution at pH 3.5 and 45° C. on PPL was 0.35 1/hr, having a doubling time of 2.9 hours.

A sample was then taken and analysed after filtration and freeze drying as FPPL-1 (FPPL Fermented Potato Protein Liquid). After $CO_2$ production as measured in the off gas was reduced to 30% of the maximum cells were harvested by centrifugation at 3880 g for 2 minutes and then the pellet was washed once with water and dried in a freeze dryer. FPPL-1 powder had a protein content of 35.5% protein determined with Dumas method. In total 115 g of FPPL dry matter was produced per kg of PPL at 53% dry matter. When extra glucose was added to balance the medium in Carbon to nitrogen ratio, an extra 20 g of FPPL dry matter could be produced which reduced ammonium content of the supernatant to zero. This is important to maximize the Potassium fertilizer value as the nitrogen content of the Potassium fertilizer should be as low as possible to have the highest value.

Example 5. Repeated Fed Batch with Filtrate Recycle

*Rasamsonia composticola* CBS 141695 was precultured in a 1 L fermenter in medium comprising 50 g/L maltodextrines and 20 g/L yeast extract and 0.5 gr/L sunflower oil and pH set at 4.5 and sterilized at 121° C. for 20 minutes. And this was inoculated with 2 ml frozen vial of inoculum material. Aeration was 0.5 L/m and stirring 1200 rpm, temperature 45° C.

5.1 First Fermentation (Potato Waste)

After 48 hours the 1 L culture was transferred to a 15 L Cplus fermenter with 2 L tapwater, 0.5 L of potato liquefact (prepared by combining 10 L potato wash water with 0.8% solids, 0.8 kg of steam peals at 11% solids (steam peals of potato) and 0.8 kg of potato sludge coming from cyclone of steam pan (6.5% solids), which was liquefied by adding ammonia to increase pH to 4.3 and 1 g of alpha amylase Fuelzyme (Verenium) and subsequently heating for 1 hour at 95° C., while stirring at 500 rpm in a Cplus fermenter of Sartorius, after 1 hr medium was cooled down to 70° C. prior to use. As the combined feedstocks were mixed, an average of 19 g dry matter per kg (1.9% dm) was present in the liquefied feedstock. 10 g. of defined medium mineral solution was added to prevent mineral shortages and 10 g/of diammoniumphosphate was added to make sure excess ammonium was present to build proteins. As titrants 12.5% ammonium and 7% of $HNO_3$ were connected to pH control pumps. Temperature was 48° C., pH set point 3.6+/−0.1 and the fermenter was aerated at 2.5 L per minute (LPM), $pO_2$>10% with stirrer 800-1500 rpm.

After 16 hours of batch growth was completed which could be observed by stabilizing and reduction of $CO_2$ production as measured in the outlet gas of the fermenter using a Bluesense $O_2$ $CO_2$ meter.

The feed was started at a rate of 2 L per hour and after having added 2.5 L of medium, the fermentation was completely blocked by the addition of the toxic liquefact (mainly toxic due to the presence of organic acids like acetic acid and lactic acid formed during the storage of the potato coproducts). To overcome the toxicity, the medium was diluted with 3 L of water and the pH was increased to 4.0 (making the organic acids less toxic). Then 4 more L of water were added after 3 L had been harvested, and pH was again reduced to 3.6 to prevent bacterial growth outbreak.

After 40 hours the mycelium had adapted to medium and feeding Liquefact at 1 L/hr was possible and so we were able to convert all the Liquefact to fungal biomass. The mycelium was harvested over a 2 mm sieve, 1 mm sieve and 0,315 mm sieve and 80% of the biomass could be harvested over the 2 mm sieve and 18% on the 1 mm sieve, 2% on the 0,315 mm sieve. The biomass from the sieves were combined and pressed to a cake of 15.5% dry matter and was labelled BSZ0174 for analysis on amino acids dry matter and crude protein. 1200 g of end of fermentation broth of potato was used to inoculate the second run using red beet.

No contamination visible under microscope yet.

5.2 Second Fermentation (Cooked Red Beet)

The potato-permeate (2840 gram) from the sieves was collected and used to suspend 3500 gram milled and cooked red beet (from Albert Heijn) (*Beta vulgaris* subsp. *vulgaris* var. *ruba*) and the 6340 gram mashed red beets were inoculated with 1200 gram broth from the potato fermentation and 4000 g of water was added to dilute the mash and to have 11540 g of starting weight with a dry matter concentration of 3.5%. Fermentation conditions were again 48 C, pH 3.6 ($HNO_3$ and $NH_3$), 2.5 L air/min, $pO_2$>10% with stirrer 800-1500 rpm.

24 hours later the broth was sieved except 1 L for the next fermentation and 2 L of broth lost due to foam out issue. 500 g cake was obtained with 21.7% dry matter and was coded BSZ0175.

No contamination under the microscope visible yet.

5.3 Third Fermentation (Raw Red Beet)

The third consecutive fermentation was carried out by adding 3000 g raw red beets (*Beta vulgaris* subsp. *vulgaris* var. *ruba*) after mashing the red beet in a kitchen machine using 2977 g of the permeate from the fermentation on red beet as dilution water. 1000 g of the red beet pulp was added to the third fermenter with 2000 g of tapwater and 1000 g of broth with mycelium from the second fermentation. 10 g of fresh baker's yeast was added in order to dose invertase as *Rasamsonia composticola* is not able to grow on sucrose (at least not in all circumstances), and these enzyme activities then has to come from the raw materials. pH set point again 3.6, temperature 48° C., 2.5 L/min aeration, $pO_2$>10% with stirrer 800-1500 rpm. After a batch phase of 10 hours, the remaining 5000 g of red beet pulp was further diluted using permeate from the second fermentation and the 7000 g of diluted feed was fed within one hour.

After 24 hours the fermented mash was sieved over 2 mm sieve (95% of dry matter harvested on 2 mm sieve and 4% on 1 mm sieve. The pressed cake was coded BSZ0176 and had 18.0% dry matter.

No contamination visual.

5.4 Fourth Fermentation

The fourth fermentation was carried to prepare for whey fermentations.

The batch medium was: 1000 g of broth from the third fermentation, 4 L permeate from the third fermentation.

pH 3.6 ($HNO_3/NH_3$), $pO_2$>10% with stirrer 800-1500 rpm, aeration 2.5 Lpm, 48° C.

Feed:

Lactose 40 g/L, defined medium mineral mix 30 g/L, diammoniumsulphate 4 g/L, pH 3.3 (sulfuric acid)

Feeding at 80 g/hr.

After 50 feeding hours 4300 g of the broth was harvested and cells were sieved over set of sieves and under the low growth rate shorter mycelium was observed and 90% of the mycelium was on the 1 mm sieve, cells do grow on defined medium with lactose as sole carbon source, and culture remains pure, no contamination visible yet.

Mycelial cake was not further processed.

5.5 Fifth Fermentation 5000 g of broth left over from the 4rth fermentation was fed with 2 kg of whole sugar beet (*Beta vulgaris* subsp. *vulgaris* var. *altissima*) milled in 4.1 L filtrate from third fermentation, 10 g fresh baker's yeast was added in order ensure sucrose conversion.

Fermentation was carried out at 50° C. as we thought some yeasts appeared in fourth fermentation. pH 3.6+/−0.1 ($HNO_3/NH_3$) aeration 2.5 Lpm, $pO_2$>10% with stirrer 800-1500 rpm, 3 ml antifoam Basildon was added.

After adding 1 L water after 20 hours of fermentation, 10 L mash was harvested partly (4 kg broth was left) the mash was sieved 80% was in 2 mm sieve, 19% in 1 mm sieve. Cake was pressed to 17.9% dm and coded BSZ0177.

Feed of fresh cheese whey from a local cheese factory with lactic acid bacteria and lactic acid in it was started at 200 g/hr, after 19 feeding hours, the feed rate was reduced to 100 g/hr because the dissolved oxygen was low.

When ammonium got <300 ppm we added diammoniumhydrogenphosphate to get $NH_3$>500 ppm.

Temperature was increased to 52° C. to see effect on mycelium length.

Whey feed was diluted 2× to reduce mycelium concentration.

After 96 hours of feeding at 600 g/hr and harvesting of 2× diluted whey, 90% of all mycelium could be harvested on the 1 mm sieve.

Next we tested again whether whey could be fermented batch wise by adding 4 L of undiluted whey to 4 L of broth at pH 3.6, fermentation was stopped which could be seen on CO2 production in off gas. Apparently the lactic acid and acetic acid was too toxic. In the broth we measured at that time 3.2 g/L of lactic acid and 0.05 g/L of acetic acid. Upon dilution with water from 8 to 12 L, fermentation recovered, and a feed with 2× diluted whey was again started. Mycelium harvested after being grown on whey was coded BSZ0178 and dry matter concentration after pressing was 19.9%.

No contamination visible under microscope anymore.

5.6 Sixth Fermentation

1 L broth from fifth fermentation was used and diluted in 5 L of water a mineral salts medium and 12 g diammoniumhydrogenphosphate with 300 g of sucrose. Fermentation was carried out at 52° C., pH 3.6+/−0.1 ($HNO_3/NH_3$) aeration 2.5 Lpm, $pO_2$>10% with stirrer 800-1500 rpm.

After 16 hours, growth rate was very low on sucrose (10 hr doubling time). 4 g of fresh baker's yeast was added to speed up the growth.

After 40 hours the broth was harvested by sieving and pressing and the sample was coded BSZ0179 and dry matter was 17.9%.

No contamination visible under microscope.

5.7 Seventh Fermentation

1 L broth from sixth fermentation was used to inoculate this fermentation and 3 L of water was used to dilute the broth, and a maltodextrin feed with 22.7 g/L maltodextrines and a mineral salts medium stock solution and 0.54 g/L diammoniumhydrogenphosphate, pH 3.4 (sulfuric acid).

The feed flow was 60 g/hr. Fermentation was carried out at 52° C., pH 3.6+/−0.1 ($HNO_3/NH_3$), aeration 2.5 Lpm, $pO_2$>10% with stirrer 800-1500 rpm.

After 16 feeding hours feed flow was increased to 80 g/hr and the feeding was continued for 5 days.

After 5 days, the fermenter broth volume was reduced to 3.75 L by taking a large harvest with 15.5% Packed Mycelial Volume (Pellet fraction after centrifugation 15 min 3880 rpm).

Next we took pig manure, sieved the manure over 2 mm sieve to remove solids. 4.6 kg pig manure was separated in 1.6 kg thick manure (not used) and 3 L thin fraction of manure containing 8933 ppm $NH_3$. The pig manure was used to feed to the fermenter When feeding 90 g/hr thin fraction of manure, the fermentation continued to produce $CO_2$ at high rate. But after 22.5 hours the remaining 1 L of thin manure was pumped in within 1 hour and then the fermentation completely stopped, indicating a toxicity of the manure when applying in high concentrations at low pH. Toxic elements in manure can be organic acids like acetic, but also valeric acid, butyric acid, propionic acid which are known to be extremely toxic at low pH, and when feeding too fast cannot be consumed and will inhibit fungal growth.

5.8 Analysis of Mycelium Composition

The mycelium harvested in the 7 above described fermentations was analysed for amino acid profile and crude protein content. The results are presented in Table 2.

Table 2 clearly indicates that the amino acid profile of the product is 1) not dependent on the raw material used, and 2) the sum of the essential amino acids is of all *Rasamsonia composticola* CBS 141695 samples (BSZ174 to BSZ179) was 16% higher than of soybean protein, while the sum of all essential amino acids of *Thermomucor indicae-seudaticae* CBS 143027 (fermentations described in Example 7 below) was even 29% higher than soybean proteins and an exceptionally high lysine content of >9% and Phenylalanine was especially high at >10% of total amino acids.

TABLE 2

Amino acid profiles of fungal biomass from fermentations as indicated

| | Rasamsonia composticola grown on | Ala % of AA | Arg % of AA | Asp/ Asn % of AA | Glu/ Gln % of AA | Gly % of AA | Pro % of AA | Ser % of AA | Cys % of AA | Tyr % of AA |
|---|---|---|---|---|---|---|---|---|---|---|
| BSZ0174 | potato | 6.4 | 5.9 | 10.5 | 12.6 | 5.1 | 4.6 | 5.6 | 0.0 | 4.3 |
| BSZ0175 | cooked and peeled red beet | 6.6 | 6.9 | 9.5 | 13.7 | 5.3 | 4.2 | 5.8 | 1.1 | 4.0 |
| BSZ0176 | fresh red beet | 7.0 | 6.2 | 9.3 | 13.2 | 5.4 | 4.7 | 6.2 | 0.0 | 3.9 |
| BSZ0177 | sugar beet | 6.7 | 6.4 | 9.7 | 13.4 | 5.4 | 4.4 | 6.0 | 0.0 | 4.0 |

TABLE 2-continued

Amino acid profiles of fungal biomass from fermentations as indicated

| | | | | | | | | | | |
|---|---|---|---|---|---|---|---|---|---|---|
| BSZ0178 | whey | 7.4 | 6.6 | 9.7 | 15.3 | 5.3 | 4.5 | 5.8 | 1.3 | 3.4 |
| BSZ0179 | sucrose | 7.1 | 6.8 | 9.8 | 13.1 | 5.5 | 4.4 | 6.0 | 0.0 | 3.8 |
| BSZ0209 | CBS 143027 on molasses 46 C., pH 3.7 | 6.4 | 6.5 | 9.5 | 12.4 | 4.5 | 3.9 | 4.8 | 1.1 | 3.8 |
| BSZ0210 | CBS 143027 on molasses 48 C., pH 3.3 | 6.2 | 6.2 | 9.0 | 11.1 | 4.3 | 3.6 | 4.9 | 1.1 | 3.7 |
| BSZ0211 | CBS 143027 on molasses 48 C., pH 3.3 | 6.4 | 5.9 | 9.2 | 12.1 | 4.5 | 3.7 | 4.9 | 1.1 | 3.8 |
| BSZ0212 | CBS 528.71 on molasses pH 3.5 and 46 C. | 7.4 | 7.3 | 9.2 | 13.2 | 5.0 | 5.0 | 4.7 | 0.9 | 3.7 |
| | *T. indicae-seudatica* strain 8 | 7.6 | 8.4 | 10.8 | 15.9 | 5.9 | 0.0 | 5.8 | 1.2 | 0.0 |
| | Soybean | 4.1 | 7.0 | 10.7 | 19.2 | 4.3 | 5.1 | 5.5 | 1.7 | 3.5 |
| | wheat | 3.8 | 5.3 | 5.8 | 24.7 | 4.1 | 9.0 | 4.5 | 1.4 | 3.0 |
| | fish | 4.3 | 4.1 | 6.2 | 9.9 | 4.5 | 3.0 | 2.8 | 0.6 | 1.9 |
| | Paecilomyces (Pekilo) | 5.7 | 5.8 | 7.8 | 10.5 | 4.5 | 5.0 | 4.3 | 0.9 | 3.1 |

| *Rasamsonia composticola* grown on | | His % of AA | Iso-leu % of AA | Leu % of AA | Lys % of AA | Met % of AA | Phe % of AA | Thr % of AA | Val % of AA | Tryp % of AA |
|---|---|---|---|---|---|---|---|---|---|---|
| BSZ0174 | potato | 3.2 | 5.4 | 8.9 | 7.0 | 2.4 | 4.0 | 5.9 | 6.7 | 1.5 |
| BSZ0175 | cooked and peeled red beet | 3.3 | 5.1 | 8.4 | 6.9 | 2.2 | 3.1 | 5.5 | 6.6 | 1.6 |
| BSZ0176 | fresh red beet | 3.5 | 5.1 | 8.2 | 8.6 | 2.3 | 2.3 | 5.8 | 6.6 | 1.6 |
| BSZ0177 | sugar beet | 3.7 | 5.0 | 8.4 | 7.7 | 2.7 | 2.7 | 5.7 | 6.4 | 1.7 |
| BSZ0178 | whey | 2.9 | 4.5 | 7.6 | 7.9 | 2.1 | 2.6 | 5.5 | 6.1 | 1.6 |
| BSZ0179 | sucrose | 3.3 | 4.9 | 8.2 | 7.9 | 2.2 | 3.0 | 5.7 | 6.6 | 1.7 |
| BSZ0209 | CBS 143027 on molasses 46 C., pH 3.7 | 3.0 | 4.9 | 8.1 | 8.3 | 2.1 | 8.6 | 4.9 | 5.7 | 1.5 |
| BSZ0210 | CBS 143027 on molasses 48 C., pH 3.3 | 3.7 | 4.5 | 7.5 | 9.0 | 1.9 | 11.7 | 4.8 | 5.4 | 1.4 |
| BSZ0211 | CBS 143027 on molasses 48 C., pH 3.3 | 3.3 | 4.7 | 8.0 | 8.2 | 2.1 | 10.4 | 4.8 | 5.7 | 1.4 |
| BSZ0212 | CBS 528.71 on molasses pH 3.5 and 46 C. | 2.4 | 4.7 | 8.1 | 7.3 | 2.4 | 6.0 | 5.2 | 5.9 | 1.4 |
| | *T. indicae-seudatica* strain 8 | 3.0 | 5.2 | 9.1 | 8.8 | 2.0 | 2.5 | 5.8 | 6.5 | 1.6 |
| | Soybean | 2.7 | 4.5 | 7.9 | 6.1 | 1.5 | 5.2 | 3.9 | 4.5 | 1.3 |
| | wheat | 1.6 | 3.4 | 6.3 | 3.5 | 1.8 | 4.3 | 3.2 | 4.4 | |
| | fish | 1.4 | 3.0 | 5.0 | 5.0 | 2.1 | 2.5 | 2.9 | 3.4 | 0.7 |
| | Paecilomyces (Pekilo) | 1.8 | 3.9 | 6.3 | 5.6 | 1.7 | 3.6 | 4.2 | 4.3 | 1.3 |

Example 6. PPL-Fermentation

Potato Protein Liquor (PPL) is a coproduct from the potato processing industry and contains large amounts of nitrogen, potassium and lactic acid resulting from growth of lactic acid bacteria in various processing steps during protein and starch extraction after which the diluted protein liquor is evaporated to a brown liquor. The PPL is not suited in animal feed because of high ashes and not preferred as fertilizer due to high concentrations of easily consumable organic matter leading to anaerobicity in the soil.

The idea was to produce a protein rich feed stock first on carbon and nitrogen and phosphate and then to filter the biomass and evaporate the Fermented PPL to produce a product that is more suitable as fertilizer (containing less easily consumable organic matter).

*Rasamsonia composticola* was propagated in a shake flask using maltodextrine (20 g/L and yeast extract 20 g/L, sunflower oil 0.5 g/L, pH 4.5) in sterile medium (121° C., 20 min), cultivated to thick mycelial culture broth at 45° C., 220 rpm for 3 days and then added to a fermenter (250 ml of inoculum culture to 4 L of medium with glucose. 1 aq 200 gr/L and 3 L water). A feed with PPL was started at 10 g/hr and linear increased to 100 g/hr in 10 hours. pH was controlled at 3.5 with 25% sulfuric acid and temperature was maintained at 45° C. while $pO_2$ was maintained >10% of saturation by aerating at 2.5 Lpm and increasing stirrer speed when needed. At 19 hours past feed start the feed was stopped and 1281 g of PPL was added. After that the fermentation was allowed to continue until all ammonia was removed from the broth.

TABLE 3

Composition of PPL before (PPL-EMS) and after (FPPL-2) fermentation

|  | PPL-EMS | FPPL-2 |
|---|---|---|
| Dry matter % | 41.8 | 43.4 |
| Ash % | 12.6 | 20.5 |
| Org matter % | 29.2 | 22.9 |
| P2O5% | 1.1 | 1.1 |
| N % | 2.4 | 1.8 |
| K2O % | 7.4 | 13 |
| K2O/N ratio | 3.1 | 7.2 |
| K2O/dm % | 7.4 | 16.6 |

The PPL was fermentable and after fermentation all biomass was sieved and pressed to an animal feed cake, the composition of which was determined and is given above in Table 2 of Example 5 with 30% crude protein on dry matter and a very nice amino acid profile.

Table 3 shows a comparison of the compositions of the PPL before fermentation with the organic potassium fertilizer (FPPL=Fermented Potato Protein Liquor). and shows that the latter was improved by more than doubling the potassium content and factor 2.5× improving Potassium per dry matter content.

Levels of glucose, lactic acid, dextrin and DP2 (Degree of Polymerisation=2, including e.g. maltose and isomaltose) were determined during fermentation (data not shown). The results demonstrate that the *Rasamsonia composticola* can co-consume lactic acid with glucose and survives by gently feeding a concentration of no more than 15 g/L lactic acid at pH 3.5. In contrast, if one starts a batch fermentation with pure PPL at pH 3.5 at 45° C. we observed no growth at all.

Example 7. Repeated Fed Batch with Intermittent Cleaning

*Thermomucor indicae-seudaticae* CBS 143027 was pre-cultured in a 2 L baffled shake flask with 250 ml medium with 50 g/L maltodextrines and 20 g/L yeast extract and 0.5 gr/L sunflower oil and pH set at 4.5 and sterilized at 121° C. for 20 minutes. This preculture was then transferred to a 15 L Cplus fermenter of Sartorius called Fermenter A with 5 L defined mineral medium with 20 g/L glucose and 2 g/L ammoniumnitrate. Temperature was 46° C. and pH 3.7+/−0.1 (7.5% NH$_3$ 4 N H$_3$PO$_4$), pO$_2$ was controlled by stirring at 900 rpm and aerating at 2.5 L/min.

After overnight growth a feed was started with molasses at a concentration of 40 g/L sugar and 2 g/L diammoniumhydrogenphosphate and a feed rate of 208 g/hr. After 5 L was fed the 10 L culture was split in two portions of 5 L in fermenter A and B. To both fermentations a molasses (same as before) feed was started at 357 g/hr. Both fermenters were aerated at 2.5 Lpm and 900 rpm, 46° C. and pH controlled at pH 3.7+/−0.1 (7.5% NH$_3$ 4 N H$_3$PO$_4$). After the feed was added all biomass of fermenter A was harvested by sieving subsequently over 2 mm, 1 mm and 0.315 mm sieves and a 0.08 μm sieve. The distribution of cake was 80%, 18%, 1%, and 1% respectively over these sieves. The cake was pressed, dried at 50° C. in fluid bed dryer to yield sample BSZ0209 (see Example 5) for Amino acid analysis. The filtrate was clear. As we saw some bacterial cocci under the microscope we acidified the B fermenter with broth to pH 2.2 using 25% sulfuric acid for 30 minutes, meanwhile we rinsed fermenter A with hot water of 70% with phosphoric acid for 20 minutes to kill bacteria in fermenter A at pH 2.2 and then split Fermenter B over Fermenter A and B so 5 L was again in both fermenters and we restarted feeding at 357 g/hr while controlling pH at pH 3.3 and temperature 48° C. After feeding to full volume after 14 hours the fermenter was further aerated for 4 more hours to consume all residual sugars and organic acids were consumed, Fermenter B was harvested and sieved.

35% of the cake was in sieve 2 mm, 70% in sieve 1 mm and 5% in smaller sieves indicating the mycelium gets shorter in the second run at pH 3.3 and 48° C. and this was pressed and dried at 50° C. to obtain sample BSZ0210 for amino acid analysis (see Table 2 in Example 5).

Fermenter B was now cleaned and acid rinsed, Fermenter A was acidified to pH 2.2 for 30 minutes and then split 50%-50% to Fermenter A and B and subsequently a third fermentation was executed at pH 3.3 and 48° C. and then pressed and dried to obtain sample BSZ0211 for amino acid analysis (see Table 2 in Example 5).

This way we can operate and keep contamination under control in principle for infinitely, but generally only have to stop on industrial scale for maintenance stop or big cleaning every 3, 6 or 12 months.

Example 8. Mechanical Dewatering of Mycelial Cake and Air-Drying

The mycelium of *Thermomucor indicae-seudaticae* CBS 143027, as harvested from the sieves of the first 2 cycles of Example 7 (i.e. sieves 2 mm and 1 mm), had a dry matter concentration of 11-15% and was subsequently pressed by hand through a lab nylon cloth to 20-30% dry matter and using a lab scale pneumatic press (Mareco Mini Pers MMP3) with adjustable time and pressure to 45-50% dry matter.

The dry matter percentages after pressing are given in Table 4, when the original cake input was 75 g at 28.0% dry matter. Table 5 shows the dry matter after pressing of *Thermomucor indicae-seudaticae* CBS 143027 after been grown on molasses or whole corn. Initial dry matter was 25%, 75 gram batches were pressed at 2 bars.

Table 6 shows the dry matter after pressing of 75 g of *Rasamsonia composticola* CBS 141695 concentrate at 2 bar when grown on molasses or milled corn. Starting from hand pressed of 26.2% dry matter. The mycelium when grown on Corn was produced by liquefying whole corn meal using amylase an alpha Fuelzyme (Weiss Biotech GmbH) at 0.2 gr/kg corn dry matter, the corn was suspended at a concentration of 5% dosage in water, pH adjusted to 4.3 using 10% sulphuric acid and 4 N NaOH and then heated to 90 C for 1 hour and cooled down to 46 prior to inoculation. pH was further adjusted to 3.6 before inoculation using 10% phosphoric acid, 2 g/L Diammoniumsulphate was added and the fermenter was inoculated with 2% full grown *Thermomucor indicae-seudaticae* inoculum CBS 143027 culture. pH was controlled at 3.6+/−0.1 using 12.5% ammonia during fermentation and pO$_2$ was maintained at >20% at all time by sparging air at 0.5 vvm and stirring at 800 rpm or higher and temperature was 46° C. After 24 hours the culture was harvested by sieving over 1 mm sieve and manual pressing over cheese cloth to 33% dry matter.

Mechanical dewatering of *Rasamsonia composticola* (grown at 50° C.) and *Thermomucor indicae-seudaticae* (grown at 46° C.) was very promising and very high levels of dry matter could be obtained both when grown on molasses (2% final sugars in 10 L broth) as when grown on corn meal (5% corn meal, 2 gr/L diammoniumphosphate). The very dry cake could be milled to a granular product by a Retch mill at 8000 rpm without a sieve. The granulate can be used as fresh animal feed ingredient, but it can easily be dried in a fluid bed dryer at 50° C. In a lab scale fluid bed dryer it was >90% dry within 30 minutes.

TABLE 4

Dry matter percentages after pressing of *Thermomucor indicae-seudaticae* CBS 143027 biomass as a function of time and pressure (grown on molasses).

| Time Pressure | 2 bar | 3.5 bar | 5 bar |
|---|---|---|---|
| 30 sec | 37.2% | 39.2% | 42.5% |
| 60 sec | 41.1% | 42.6% | 45.6% |
| 120 sec | 51.4% | 46.2% | 48.8% |

TABLE 5

Comparison of percentages dry matter of *Thermomucor indicae-seudaticae* CBS 143027 biomass grown on molasses or whole corn as a function of pressing time.

| time (min) | Molasses | Corn |
|---|---|---|
| 0.0 | 25.3% | 33.0% |
| 0.5 | 43.6% | 44.2% |
| 1.0 | 46.1% | 45.6% |
| 1.5 | 47.5% | 45.7% |
| 2.0 | 47.5% | 45.2% |
| 3.0 | 48.0% | 46.9% |
| 5.0 | 47.9% | 49.4% |

TABLE 6

Comparison of percentages dry matter of *Rasamsonia composticola* CBS 141695 biomass grown on molasses or whole corn as a function of pressing time.

| time (min) | Molasses | Corn |
|---|---|---|
| 0.0 | 26.2% | 30.0% |
| 0.5 | 37.1% | 40.6% |
| 1.0 | 40.9% | 44.2% |
| 1.5 | 42.3% | 45.4% |
| 2.0 | 42.7% | 46.3% |
| 3.0 | 46.5% | 48.5% |
| 5.0 | 46.1% | 47.3% |

Example 9. Alternative Strains

A set of alternative strains tested for being suitable alternative for making SCP at high temperature and low pH. Part of the strains was isolated from a Dutch compost obtained from Van lersel Biezenmortel BV. By adding 100 g of compost to 1 L water, mixing it thoroughly for 30 min, sieving it over 2 mm sieve, and then adding to 6 L medium in a Cplus fermenter with 0.5% Fibrex 500 (sugar beet pulp fibre), 0.5% wheat bran, 0.5%, cellulose BH200 0.5% and maltodextrin 0.5% and 2 g/L diammoniumsulphate. A mineral medium a mineral solution containing sufficient K, P, S, Ca, Mg, Zn, Fe, Mn, Cu for good fungal growth (US20020039758), and the fermenter was aerated at 3 L per minute and 100 mbar overpressure, 500 rpm, 50° C., pH 3.6 (Controlled with diluted phosphoric acid and 12.5% ammonium). The fermenter was run for 1 week and temperature and pH were modified between 50 and 60° C. and pH was changed between 2.7 and 3.2 in various combinations. Fungi were plated in serial dilutions up to $10^{-6}$ and plated on OGYE agar medium obtained from Tritium microbiologie in Eindhoven. After growing plates 2 days at 48° C., the most prominent fungi on the highest dilutions were picked, colonies restreaked, and the identity was determined using PCR amplification and sequencing services from Base Clear with their ITS fungal identity determination. Genomic DNA was extracted using the ZR Fungal/Bacterial DNA Microprep kit (D6007). One single PCR amplification reaction was run with primer set ITS1-PCR, ITS5-PCR, ITS1-F-PCR, SR6R-PCR and fungi-28s-UNIR (Table 7). The obtained amplicon was sequenced in six different reactions, each reaction with a different primer. The primers used for Sanger sequencing are described in Table 8. The six sequenced strands per strain were nucleotide BLASTed in the NCBI database for corresponding sequences.

TABLE 7

PCR primers used for ITS amplification.

| ITS1-PCR | TCCGTAGGTGAACCTGCGG |
|---|---|
| ITS5-PCR | GGAAGTAAAAGTCGTAACAAGG |
| ITS1-F-PCR | CTTGGTCATTTAGAGGAAGTAA |
| SR6R-PCR | AAGTAAAAGTCGTAACAAGG |
| fungi-28s-UNIR | GGTCCGTGTTTCAAGACG |

TABLE 8

The primers used for Sanger sequencing.

| ITS2-SEQ | GCTGCGTTCTTCATCGATGC |
|---|---|
| ITS3-SEQ | GCATCGATGAAGAACGCAGC |
| ITS4-PCR | TCCTCCGCTTATTGATATGC |
| ITS5-PCR | GGAAGTAAAAGTCGTAACAAGG |
| Fungi-28s-UNIF | GGTCCGTGTTTCAAGACG |
| Fungi-28s-UNIR | GCATATCAATAAGCGGAGGAAAAG |

6 isolates were obtained and were determined as:

*Rasamsonia emersonii* (1701-3-7)

*Thermomucor indicae-seudaticae* (isolate 11)

*Thermomucor indicae-seudaticae* (1701-1-2)

*Rhizomucor miehei* (1701-1-9)

*Rhizomucor pusillus* Isolate 13

*Rhizomucor pusillus* Isolate 12

Next to this a number of thermophylic fungal strains were ordered from CBS to screen the strains, together with some of our own isolates, for growth at high temperature and low pH, sievable morphology and the production of high amounts of protein (42° C. in medium with Glucose 1%, Yeast extract 4%, 3 days shaking at 220 rpm and harvesting by filtration, washing mycelium with water and freeze dried to >98% dry matter). The results are summarized in Table 9.

TABLE 9

Properties of thermophylic fungal strains

| Strain | CBS code | High temp | Low pH | Sievable morphology | Protein % of dm |
|---|---|---|---|---|---|
| Rasamsonia composticola | 141695 | ++ | ++ | + | 36.9 |
| Talaromyces emersonii | 393.64 | + | + | + | 33.5 |
| Rasamsonia emersonii 1701-3-7 | 143030 | + | + | + | 33.0 |
| Rhizomucor miehei (Isol wim) | – | + | – | + | 46.9 |
| Rhizomucor miehei (1701-1-9) | 143029 | + | + | + | 45.8 |
| Rhizomuror pusillus Isolate 12 | – | + | + | + | 48.2 |
| Rhizomucor pusillus isolate 13 | 143028 | + | + | + | 51.6 |
| Thermomucor indicae-seudaticae (isolate 11) | 143027 | + | + | ++ | 39.6 |
| Thermomucor indicae-seudaticae (1701-1-2) | – | + | +/– | + | 33.1 |
| Thermomyces lanuginosus | 632.91 | – | – | – | 45.8 |
| Thermomucor indicae-seudatica | 104.75 | + | + | + | 26.7 |
| Thermoascus thermophilus | 528.71 | + | + | +/– | 39.8 |
| Myceliophthora heterothallica | 202.75 | tbd | | | |
| Thielava terrestris | 546.86 | tbd | | | |
| Chaetomium thermophium var thermophilum | 144.50 | nd | Nd | nd | nd |
| Humicola grisea var grisea | 119.14 | – | – | nd | nd |
| Paecilomyces marquandii | 106.85 | – | – | nd | nd |
| Thermothelomyces thermophila or Myceliophthora thermophila | 117.65 | + | + | + | 45.0 |
| Thielava terricola var. minor | 611.74 | + | + | +/– | 56.8 |
| Myriococcum thermophilum | 389.93 | +/– | +/– | ? | 36.3 |
| Acremonium thermophilum | 734.71 | +/– | +/– | ? | 46.1 |
| Thermophymatospora fibuligera | 531.94 | +/– | +/– | ? | 45.7 |

Nd = not determined

Some strains were retested on 15 L scale fermenters for evaluation of biomass yield, protein content and amino acid profile. Cane molasses were used as carbon source supplemented in C limitation (glucose<2 g/L, $NH_3$>500 ppm) with 2 g/L diammmmoniumphosphate in feed and cane molasses was fed to the fermenter to a final concentration of 2% sugar when growing at various pH and temperature. $pO_2$ controlled at >10%, pH controlled using 4 N $H_3PO_4$ and 12.5% $NH_3$. In case of Rasamsonia composticola, fermentation on cane molasses 0.5 gr/L of active dried yeast was added to the batch medium, as Rasamsonia composticola does not grow fast on sucrose as it lacks invertase activity, and acid hydrolysis of sucrose might be too slow. A typical yield of biomass dry matter on sugars was approximately 0.5 g dry matter per g sugar and >99% of biomass could be harvested by sieving over 1 mm sieve. The results are summarized in Table 10.

TABLE 10

Fermentation of selected thermophylic fungal strains on cane molasses.

| | Temp ° C. | pH | Protein (% of dm) | Remark |
|---|---|---|---|---|
| Rasamsonia composticola CBS 141695 | 48 | 3.5 | 35.8 | |
| Rhizomucor pusillus isolate 13 | 48 | 3.7 | 42.9 | 7 L Bubble column at 1 vvm of air |
| Thermomucor indicae-sedeudaticae isolate 11 | 46 | 3.7 | 49.8 | |
| Thermomucor indicae-sedeudaticae isolate 11 | 46 | 3.7 | 43.5 | |
| Thermomucor indicae-sedeudaticae isolate 11 | 48 | 3.3 | 38.9 | |
| Thermoascus thermophilus CBS 528.71 | 46 | 3.7 | 35.3 | Sample BSZ0212 for amino acid analysis (see Table 2 Example 5) |

Example 10. Growing Thermophylic Fungi on Waste Water Sludge and Dewatering without Flocculants Rasamsonia composticola CBS 141695 was pre-grown in lab scale in 2 L Erlenmeyers with 250 ml medium based on toilet paper as sole carbon source (10 gr/L and ammonium sulphate 2 gr/L supplemented with a mineral medium as known in the art, pH was adjusted to 4 and the medium was sterilized at 121° C. 20 minutes. After cooling down the flask was inoculated and incubated for 2 days at 48° C. The full grown culture was then transferred to a 7 L bubble column with 7 L Primary waste water sludge at 8 gr/L dry matter and the bubble column was aerated at 0.3 vvm and the temperature was maintained at 48° C. and pH 3 (Phosphoric acid 4 N). The medium was cultivated for two weeks and 2 L per day were harvested and supplemented with fresh sludge. The 2 L of fermented sludge was then filtered over the 1 mm sieve and the cake was pressed over de Mareco minipress MMP3. A cake with 45% dry matter could be obtained in this way without adding flocculants.

Example 11. Fermentation of Corn with *Thermomucor*, Harvesting Mycelium and Ferment the Filtrate with a Second Organism *Rasamsonia* to Increase Yield Preculture Conditions Fungal cultures frozen of strain *Thermomucor indicae-seudaticae* CBS 143027 and strain *Rasamsonia composticola* CBS 141695 at −85° C. were thawed and used to inoculate baffled shake flasks with 250 mL of YG liquid medium (20 g $L^{-1}$ glucose, 20 g $L^{-1}$ yeast extract, pH 4.5 adjusted with $H_2SO_4$/NaOH), sterilized at 121° C. for 15 min. Cultures were incubated until fully-grown (approximately 3 days) at 42° C. with shaking at 180 rpm.

Growth Medium

For the growth of strain CBS 143027 on corn, 500 g of cornmeal were dissolved in 9500 g of water (5% w/w). For starch liquefaction of this solution, 0.2 mL of the commercial endo-α-amylase FuelZyme® LF (WeissBioTech, Germany) were added. Liquefaction was performed at pH 4.5 (adjusted with $H_3PO_4$) and 90° C. for 3 hours. After this, temperature was decreased to 46° C. and $(NH_4)_2HPO_4$ was added to a final concentration of 2 g $L^{-1}$. pH was then adjusted to pH 3.5 using $H_3PO_4$.

Cultivation of Strain CBS143027

487 g of fully grown preculture of strain *Thermomucor indicae-seudaticae* CBS 143027 were used to inoculate the corn medium. Cultivation was performed in a 15-liter BIOSTAT® Cplus fermenter (Sartorius Stedim Biotech, Bangalore, India) at a pressure of 100 bar, agitation of 500 rpm, air inflow of 5 L min-1 (vvm=0.5) and 46° C. pH was continuously adjusted to pH 3.50 during the fermentation using 12.5% ammonia and 20% w/w $H_3PO_4$. Concentration of $O_2$ and $CO_2$ was continuously measured in the off-gas. If dissolved oxygen was lower than 30% of the saturation value, stirring speed was automatically increased to keep it higher than this threshold. Antifoam (sunflower oil) was added at a rate of 1 g $h^{-1}$ during the entire duration of the cultivation.

Harvesting *T. Indicae-Seudaticae* Biomass and Inoculation of Next Fermentation with *R. Composticola*

After 46 hours of cultivation, the content of the reactor was harvested and sieved using metal sieves with pore diameters of 2, 1, 0.315 and 0.180 mm. Cakes in each one of the sieves was weighted and hand-pressed using a cheesecloth filter. The filtrate of both steps was weighted and kept for the next cultivation cycle using strain *Rasamsonia composticola* CBS141695. Before starting this cultivation, the walls of the fermenter were washed with water to remove biomass that could not be initially removed via standard harvesting.

The filtrate of the first cultivation cycle with 1.1% and had was put back into the fermenter and was inoculated with 479 g of fully grown preculture of strain *Rasamsonia composticola* CBS141695. The cultivation conditions were: 100 bar, air inflow of 5 L $min^{-1}$, agitation of 1000 rpm, 48° C. and pH of 3.20. Antifoam was also continuously added at 1 g $h^{-1}$. The full content of the fermenter was harvested after 45 hours of growth.

Results

*Thermomucor indicae-seudaticae* grew well in nontoxic whole corn medium at 5% dry matter. After 46 hours of cultivation on corn medium, 10.05 kg of culture were harvested and sieved. Sieving resulted in 2252 g of wet cake, most of which 98% was separated with the 1 (18%) and 2 mm (80%) metal sieves. To remove more liquid from this cake, it was filtered using a cheesecloth. This resulted in a 682 g of cake with a dry matter content of 32.0%. In total 218.2 gr of dry mycelium was harvested.

8994 g of filtrate were recovered from the sieving and the cheesecloth filtering, with a dry matter content of 1.10%±0.18%. This filtrate had a pH of 3.12 and ammonia concentration of 430 ppm. The fact that the filtrate had 1.1% dry matter suggests that some sugars and/or other soluble substrates are not consumed efficiently. If this is the case, improvement of the process could be achieved by growth of a wider or different-substrate-range strain on this filtrate from the first fermentation.

8336 g of the filtrate from the *Thermomucor* fermentation were used as medium for the growth of *Rasamsonia composticola*. After 45 hours of cultivation, 8.03 kg of culture were harvested. Sieving took place over 4 sieves with 2 mm, 1 mm, 0.315 mm and 0.18 mm respectively and harvested were collected resulted in 911 g of wet cake at 5.69% dm. The biomass yield was 51.9 gr dry matter. Filtrate now contained 0.86% dm.

The total biomass yield of the overall process is now 218.2 gr *Thermomucor*+51.9 gr of *Rasamsonia* which means in total 270.1 gr dry mycelium out of 500*0.88=440 gr of corn dry matter gives a yield of 0.61 gr dry SCP at high protein per gr of corn dry matter put into the process.

Adding a second step increases the biomass yield with 24% and the dry matter in the filtrate is reduced by 22%.

Example 12. Isolation and Adaptation of *Rhizopus* sp. to Acidic Conditions and High Temperature A *Rhizopus* strain was isolated from a commercial Tempeh starter, by plating on OGYE agar and incubation at 37° C. in hood. For taxonomic identification of the strain genomic DNA was isolated and the internal transcribed spacer (ITS) region were amplified and sequenced. The ITS fragments were amplified using the primers 5'-TGCCAGTAGTCATATGCTTGT'3 (Euk20f; Forward) and 5'-ACCAGACTTGTCCTCCAAT-'3 (Reverse) (Integrated DNA Technologies). Sanger sequencing was performed by BaseClear (Leiden, the Netherlands), using the same primers used for the amplification of the ITS. The sequencing results obtained with the forward primer are presented as SEQ ID No: 13 and those obtained with the reverse primer are presented as SEQ ID No: 14. When these sequences were blasted to the NCBI database, no single *Rhizopus* species was found with 100% identity and 100% coverage. Percentages identity of 99-100% with 96-98% coverage were found for *Rhizopus oryzae, Rhizopus chlamydosporus, Rhizopus microsporus, Rhizopus stolonifer* and *Mucor indicus*.

The strain was subsequently grown in shake flasks containing a medium for fungal growth (US20020039758) with sufficient K, P, S, Ca, Mg, Zn, Fe, Mn, Cu to which 2 g/L $NH_4NO_3$, 1.7 g/L Yeast Nitrogen Base (without Nitrogen source) and 20 g/L glucose was added. The pH was adjusted to pH 3.5 by adding $H_2SO_4$ and/or NaOH. 35 ml of this medium was added to baffled Erlenmeyer flask and sterilized for 15 minutes at 121° C.

The isolate was then adapted to higher temperatures by increasing the growth temperature after every consecutive transfer (1 ml into the next 35 ml medium). The transfer took place after a thick culture was obtained by visual inspection (usually after 2-3 days) when shaking the culture at 220 rpm, 2.5 cm stroke. After growing at pH 3.5 and 46° C. with a doubling time of less than 15 hours, the strain was deposited as CBS 143160.

The invention claimed is:

1. A process for producing single cell protein (SCP), the process comprising the steps of:
   a) growing a thermophilic fungus of the species *Rhizomucor pusillus* in a medium containing a fermentable carbon-rich feedstock; wherein the fungus is grown in submerged culture under non-sterile conditions at a temperature higher than 45° C. and a pH of less than 3.8; and,
   b) recovering SCP from the medium in the form of biomass of the thermophilic fungus grown in step a) wherein the protein content of the biomass is at least 40% (w/v) on dry matter basis.

2. The process according to claim 1, wherein the thermophilic fungus is *Rhizomucor pusillus* CBS 143028.

3. The process according to claim 1, wherein the process is a fed-batch process, a repeated fed-batch process or a continuous process.

4. The process according to claim 3, wherein the process is a carbon-limited process.

5. The process according to claim 4, wherein the rate at which the feedstock is fed into a fermenter is in the range of 0.05 to 0.2 1/hr.

6. The process according to claim 1, wherein the fermentable carbon-rich feedstock is one or more of a by-product or waste from agriculture or food production, silage, and a product of plant origin that is compatible for food application.

7. The process according to claim 1, wherein the fermentable carbon-rich feedstock is one or more of sugar beet pulp, liquid C-starch from grain processing, vegetable waste from production of peeled or cut vegetables, rejected vegetables, Palm mill residues, palm oil mill effluent (POME), empty fruit bunches (EFB), palm fronds, corn, potato, wheat, rice, cassava, sugar cane, sugar cane juice, sugar beet, sugar beet juice, thick juice, molasses, cane molasses, glucose syrups, fructose syrups and vegetable oils.

8. The process according to claim 1, wherein the medium contains a nitrogen source comprising one or more of ammonia, urea and nitrate.

9. The process according to claim 1, wherein the carbon-rich feedstock comprises organic acids and wherein in step a) the concentration of the carbon-rich feedstock is below a concentration at which the toxicity of the organic acids in the feedstock reduce the growth rate of the fungus.

10. The process according to claim 9, wherein the carbon-rich feedstock is fed to the medium at a rate at which the concentration of the carbon-rich feedstock is kept below the concentration at which the toxicity of the organic acids in the feedstock reduces the growth rate of the fungus.

11. The process according to claim 10, wherein the concentration at which the toxicity of the organic acids in the feedstock reduces the growth rate of the fungus is defined as the highest concentration of the carbon-rich feedstock which does not cause a reduction in at least one of the rate of $CO_2$ production and the rate of $O_2$ consumption by the fungus.

12. The process according to claim 9, wherein the carbon-rich feedstock in the medium is at a concentration of, or is fed to the medium at a rate to maintain a concentration of less than 5% (w/v) dry matter.

13. The process according to claim 1, wherein the biomass is recovered from the medium by at least one of sieving, filtration and decantation to obtain a sieved, filtered or decanted biomass cake.

14. The process according to claim 13, wherein the dry matter concentration of the sieved, filtered or decantated biomass cake is at least 12% (w/v).

15. The process according to claim 13, wherein the biomass is recovered from the medium by at least one of rotating drum filtration, a filter press, a belt filter, a screen, a sieve, a sieve belt, a DSM screen, a belt press, a screw press and a decanter centrifuge.

16. The process according to claim 13, wherein the biomass cake is further dried by pressing residual water out.

17. The process according to claim 13, wherein the biomass cake is further dried by pressing residual water out, wherein the particle size of the biomass cake is reduced by at least one of extrusion and milling, and wherein the extruded or milled cake is dried.

18. The process according to claim 17, wherein the extruded or milled cake is dried at a temperature in the range of 30-70° C.

19. The process according to claim 17, wherein the extruded or milled cake is dried in a belt dryer or in a fluid bed dryer.

* * * * *

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
tccgtaggtg aacctgcgg                                                    19

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ggaagtaaaa gtcgtaacaa gg                                                22

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
cttggtcatt tagaggaagt aa                                                22

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
aagtaaaagt cgtaacaagg                                                   20

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
ggtccgtgtt tcaagacg                                                     18

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gctgcgttct tcatcgatgc                                                   20

<210> SEQ ID NO 7
<211> LENGTH: 20
<212> TYPE: DNA
<213> ORGANISM: Artificial Sequence

```
<220> FEATURE:
<223> OTHER INFORMATION: Primer

<400> SEQUENCE: 7
gcatcgatga agaacgcagc                                                 20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tcctccgctt attgatatgc                                                 20

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
ggtccgtgtt tcaagacg                                                   18

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
gcatatcaat aagcggagga aaag                                            24

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
tgccagtagt catatgcttg t                                               21

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
accagacttg tcctccaat                                                  19

<210> SEQ ID NO 13
<211> LENGTH: 523
<212> TYPE: DNA
<213> ORGANISM: Rhizopus sp.

<400> SEQUENCE: 13
cskksmgkgt ymywaggtat aaataacttt atattgtgaa actgcgaatg gctcattaaa     60
tcagttatga tctacgtgac aaattcttta ctacttggat aaccgtggta attctagagc    120
```

```
taatacatgc aaaaaagccc tgacttacga aggggtgcac ttattagata aaaccaacgc      180
ggggtaaaac ctgtttcttg gtgaatcata ataattaagc ggatcgcatg gccttgtgcc      240
ggcgacggtc cactcgattt tctgccctat catggttgag attgtaagat agaggcttac      300
aatgcctaca acgggtaacg gggaattagg gttcgattcc ggagagggag cctgagaaac      360
ggctaccaca tccaaggaag gcagcaggcg cgcaaattac ccaatcccga cacggggagg      420
tagtgacaat acataacaat gcagggcctt taaggtcttg caattggaat gagtacaatt      480 taaatcccctt aacgaggatc aattggagga caagtctggt aaa                       523

<210> SEQ ID NO 14
<211> LENGTH: 520
<212> TYPE: DNA
<213> ORGANISM: Rhizopus sp.

<400> SEQUENCE: 14
aggcattaat tgtactcatt ccaattgcaa gaccttaaag gccctgcatt gttatgtatt       60
gtcactacct ccccgtgtcg ggattgggta atttgcgcgc ctgctgcctt ccttggatgt      120
ggtagccgtt tctcaggctc cctctccgga atcgaaccct aattccccgt taccgttgt      180 aggcattgta agcctctatc ttacaatctc aaccatgata gggcagaaaa tcgagtggac      240
cgtcgccggc acaaggccat gcgatccgct taattattat gattcaccaa gaaacaggtt      300
ttaccccgcg ttggttttat ctaataagtg caccccttcg taagtcaggg cttttttgca      360
tgtattagct ctagaattac cacggttatc caagtagtaa agaatttgtc acgtagatca      420
taactgattt aatgagccat tcgcagtttc acaatataaa gttatttata cttagacatg      480
catggcttaa tctttgagac aagcatatgc ttwactggca                            520
```